United States Patent
Sato et al.

(10) Patent No.: US 8,282,633 B2
(45) Date of Patent: Oct. 9, 2012

(54) HIGH-FREQUENCY SURGICAL APPARATUS AND HIGH-FREQUENCY SURGICAL METHOD FOR CLOSURE OF PATENT FORAMEN OVALE

(75) Inventors: Taisuke Sato, Hachioji (JP); Manabu Ishikawa, Hachioji (JP)

(73) Assignee: Olympus Medical Systems Corp. (JP)

( * ) Notice: Subject to any disclaimer, the term of this patent is extended or adjusted under 35 U.S.C. 154(b) by 642 days.

(21) Appl. No.: 12/484,650

(22) Filed: Jun. 15, 2009

(65) Prior Publication Data

US 2010/0318081 A1 Dec. 16, 2010

(51) Int. Cl.
*A61B 18/12* (2006.01)
(52) U.S. Cl. .......................................... 606/41
(58) Field of Classification Search .............. 606/41
See application file for complete search history.

(56) References Cited

U.S. PATENT DOCUMENTS

| 2005/0192654 A1* | 9/2005 | Chanduszko et al. ......... 607/116 |
| 2007/0123852 A1* | 5/2007 | Deem et al. ..................... 606/45 |
| 2008/0140070 A1* | 6/2008 | Filloux et al. ................... 606/41 |

FOREIGN PATENT DOCUMENTS

| JP | 2003-503103 | 1/2003 |
| JP | 2003-504108 | 2/2003 |
| JP | 2006-521181 | 9/2006 |
| JP | 2008-503269 | 2/2008 |
| WO | WO 99/18870 | 4/1999 |
| WO | WO 01/00114 A1 | 1/2001 |
| WO | WO 01/03594 A1 | 1/2001 |
| WO | WO 2004/086944 A2 | 10/2004 |
| WO | WO 2006/009586 A1 | 1/2006 |
| WO | WO 2006/009856 A1 | 1/2006 |
| WO | WO 2007/100067 | 9/2007 |

* cited by examiner

*Primary Examiner* — Michael Peffley
*Assistant Examiner* — Daniel Fowler
(74) *Attorney, Agent, or Firm* — Ostrolenk Faber LLP

(57) ABSTRACT

A high-frequency surgical apparatus for treating patent foramen ovale in a heart includes a flexible probe which has such a length as to allow the probe to be placed in the patent foramen ovale by passing through the blood vessel; an electrode section which, being placed at a distal end of the probe, has three or more electrodes along a longitudinal direction of the probe; a high-frequency power supply section which supplies predetermined high-frequency power to the patent foramen ovale via the electrode section; a switching section which switches among a plurality of signal lines connected to the three or more electrodes; and a high-frequency power control section which controls switching of the switching section so as to supply the high-frequency power to two electrodes.

6 Claims, 17 Drawing Sheets

HIGH-FREQUENCY SURGICAL APPARATUS AND HIGH-FREQUENCY SURGICAL METHOD FOR CLOSURE OF PATENT FORAMEN OVALE

BACKGROUND OF THE INVENTION

1. Field of the Invention

The present invention relates to a high-frequency surgical apparatus and to a high-frequency surgical method for closure of patent foramen ovale, where the high-frequency surgical apparatus and high-frequency surgical method are used to perform high-frequency surgery by applying a high-frequency current to the living tissues of patent foramen ovale in the heart.

2. Description of the Related Art

Generally, high-frequency surgical apparatus are known which cause living tissues adhere to each other using high-frequency power. When high-frequency power is applied to living tissues from such a high-frequency surgical apparatus, Joule heat generated by a high-frequency current flowing through the living tissues heats the living tissues. The living tissues have the property of denaturing and consequently adhering to each other when heated sufficiently.

There is a condition known as patent foramen ovale (PFO) in the heart. The PFO is a flaplike gap existing in part of the atrial septum which separates the left atrium from the right atrium. Normally, the pressure in the left atrium is higher than the pressure in the right atrium, so that the valvula foraminis ovalis is pressed against the atrial septum, and thereby the PFO is closed. However, severe coughing or tension (due to pressure on the lungs) can reverse the pressure difference, temporarily opening the flap.

Blood may contain blood clots developed in the body. Normally, the blood returning to the right atrium from the body is sent to the lungs where a blood clot is removed. However, it may happen that the instant the PFO opens, a blood clot that flow into the right atrium passes through the PFO and is sent back into the body. If the blood clot reaches the brain, it can cause cerebral infarction. Thus, it is desirable to close the PFO.

A conventional technique, International publication No. WO 2007/100067 discloses a high-frequency surgical apparatus used to close a PFO. The conventional technique includes grasping means made up of a needle member and grasping member. Both the needle member and grasping member act as high-frequency electrodes. After a PFO is grasped with the two members, high-frequency power is applied to the two electrodes to heat the PFO by Joule heat and thereby close the PFO.

SUMMARY OF THE INVENTION

In one aspect, the present invention provides a high-frequency surgical apparatus for treating patent foramen ovale in a heart, including: a probe which, being configured to be flexible, has such an outside diameter as to allow the probe to be inserted in a blood vessel communicated with the patent foramen ovale and such a length as to allow the probe to be placed in the patent foramen ovale by passing through the blood vessel; an electrode section which, being placed at a distal end of the probe, has three or more electrodes along a longitudinal direction of the probe; a high-frequency power supply section which supplies predetermined high-frequency power to living tissue of the patent foramen ovale via the electrode section; a switching section which switches among a plurality of signal lines connected to the three or more electrodes to supply high-frequency power from the high-frequency power supply section to at least two of the three or more electrodes; and a high-frequency power control section which controls switching of the switching section so as to supply the high-frequency power to at least two electrodes in the electrode section.

In one aspect, the present invention provides a high-frequency surgical method for closure of patent foramen ovale, the high-frequency surgical method using a high-frequency probe to close the patent foramen ovale in a heart by application of high-frequency power, including: a step of inserting the high-frequency probe into a blood vessel and placing an electrode section at a distal end of the high-frequency probe between the atrial septum and valvula foraminis ovalis, the atrial septum and the valvula foraminis ovalis being living tissues of the patent foramen ovale in the heart; a step of selecting at least two electrodes out of three or more electrodes in the electrode section, which are formed along a longitudinal direction of the high-frequency probe, and supplying high-frequency power to the selected electrodes; and a step of selecting another combination of the electrodes at least once and supplying high-frequency power to the selected electrodes.

In one aspect, the present invention provides a high-frequency surgical method for closure of patent foramen ovale, the high-frequency surgical method using a high-frequency probe to close the patent foramen ovale in a heart by application of high-frequency power, including: a penetrating step of causing a distal end of the high-frequency probe passed through a blood vessel to penetrate at least valvula foraminis ovalis; a flexing step of flexing a flexing section installed near the distal end of the high-frequency probe by operating from a proximal end of the high-frequency probe; a hauling step of hauling the high-frequency probe toward a proximal side with the flexing section kept flexed; and a supplying step of selecting at least different combinations of electrodes, a plurality of times, from among three or more electrodes installed at the distal end of the high-frequency probe and supplying high-frequency power for treatment to the selected electrodes.

In one aspect, the present invention provides a high-frequency surgical method for closure of patent foramen ovale, the high-frequency surgical method using a high-frequency probe to close the patent foramen ovale in a heart by application of high-frequency power, including: a puncturing step of puncturing valvula foraminis ovalis adjacent to the atrial septum with a distal end of the high-frequency probe from the atrial septum for treatment by the application of high-frequency power; a penetrating step of causing the high-frequency probe to penetrate the atrial septum and the valvula foraminis ovalis; a flexing step of flexing a flexing section installed near the distal end of the high-frequency probe by operating from a proximal end of the high-frequency probe; a hauling step of hauling the high-frequency probe toward a proximal side with the flexing section kept flexed; and a supplying step of selecting at least different combinations of electrodes, a plurality of times, from among three or more electrodes installed at the distal end of the high-frequency probe and supplying high-frequency power for treatment to the selected electrodes.

BRIEF DESCRIPTION OF THE DRAWINGS

FIG. 1 is an overall configurational diagram of a high-frequency surgical apparatus according to the first embodiment of the present invention;

FIG. 2 is a diagram showing a structure on a distal side of a high-frequency probe;

FIG. 3 is a block diagram showing an internal configuration of a high-frequency power supply system of the high-frequency surgical apparatus;

FIG. 4 is an explanatory diagram showing an area around PFO in the heart;

FIG. 5 is a diagram showing a chase where an electrode section at a distal end of the high-frequency probe is placed in PFO;

FIG. 6 is a diagram showing a situation when high-frequency power is supplied to electrodes of the high-frequency probe under conditions shown in FIG. 5; and FIG. 7 is a flowchart showing procedures for high-frequency surgery.

FIG. 8 is an overall configurational diagram of a high-frequency surgical apparatus according to the second embodiment of the present invention;

FIG. 9 is a diagram showing a structure on a distal side of a catheter;

FIG. 10 is a block diagram showing an internal configuration of a high-frequency power supply system of the high-frequency surgical apparatus;

FIG. 11 is a flowchart showing procedures of a high-frequency surgical method;

FIG. 12 is a diagram schematically showing a state where a high-frequency probe is placed in close contact with PFO using a ring-shaped member on the distal side of the catheter; and FIG. 13 is a flowchart showing part of procedures of a high-frequency surgical method according to a variation of the second embodiment of the present invention.

FIG. 14 is an external view showing a high-frequency probe according to the third embodiment of the present invention;

FIG. 15 is a sectional view showing an internal structure of the high-frequency probe;

FIG. 16 is a sectional view showing the high-frequency probe as the high-frequency probe is flexed;

FIG. 17 is a flowchart showing procedures of a high-frequency surgical method according to the third embodiment;

FIG. 18 is an explanatory diagram showing a situation where PFO is treated from the side of valvula foraminis ovalis using the high-frequency probe penetrating the atrial septum and the valvula foraminis ovalis;

FIG. 19 is a diagram showing a situation where PFO is treated using a high-frequency probe penetrating the valvula foraminis ovalis;

DETAILED DESCRIPTION OF THE PREFERRED EMBODIMENTS

Embodiments of the present invention will be described below with reference to the drawings.

First Embodiment

A first embodiment of the present invention will be described below with reference to FIGS. 1 to 7.

Figure 1:
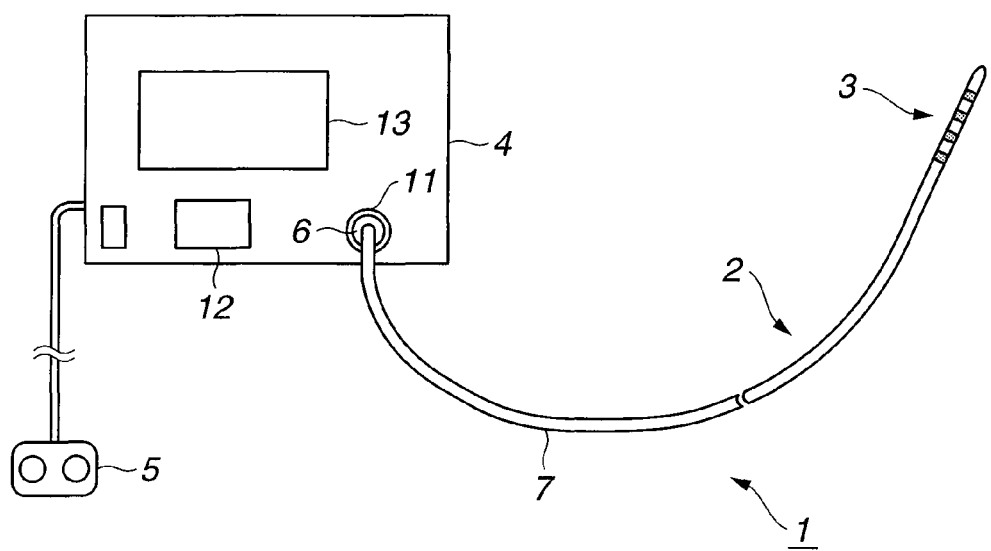
FIGS. 1 to 7 relate to a first embodiment of the present invention, where.

As shown in FIG. 1, a high-frequency surgical apparatus 1 according to the first embodiment of the present invention has a high-frequency probe 2 as a high-frequency treatment instrument used to perform high-frequency surgery on patent foramen ovale (PFO) in the heart of a patient.

The high-frequency surgical apparatus 1 is detachably connected with a rear end (proximal end) of the high-frequency probe 2 and is equipped with a high-frequency power supply system 4 to supply high-frequency power for high-frequency surgery to an electrode section 3 installed at a distal end (tip) of the high-frequency probe 2. The high-frequency power supply system 4 is connected with a foot switch 5 in order for a surgeon to supply and stop high-frequency power.

A connector jack 11 is installed on a front face of the high-frequency power supply system 4 in order to be detachably connected with a connector 6 at the rear end (proximal end) of the high-frequency probe 2.

Figure 2:
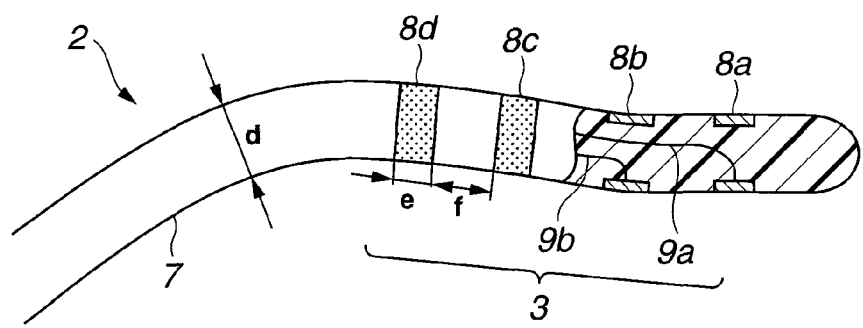

FIG. 2 shows the high-frequency probe 2. The high-frequency probe 2 has a flexible shaft 7 small enough in outside diameter d to be inserted in a blood vessel (described later) and long enough to treat PFO through the blood vessel from outside the body.

The shaft 7 of the high-frequency probe 2 is, for example, cylindrical in shape and is made, for example, of flexible material such as fluoroplastics which feature good electrical insulation and small high-frequency losses.

At a distal end of the shaft 7, three or more electrodes (four electrodes 8a, 8b, 8c, and 8d in a concrete example in FIG. 2) which make up the electrode section 3 are installed along a longitudinal direction. Incidentally, the number of electrodes is not limited to four.

Each electrode 8$i$ ($i$=a, b, ..., d) is formed, for example, as an annular metal member fitted over a recess formed on an outer periphery of the shaft 7 in such a way as to be exposed on a surface of the shaft 7.

Also, each electrode 8$i$ has, for example, a predetermined length e. An interval between adjacent electrodes is f.

Also, each electrode 8$i$ is connected to one end of a lead wire 9$i$ which serves as a signal line by being inserted in the shaft 7. The other end (proximal end) of the lead wire 9$i$ is connected to switching sections 23a and 23b in the high-frequency power supply system 4 via the connector 6 and connector jack 11 as shown in FIG. 3.

As shown in FIG. 1, a setting section 12 and display section 13 as well as a power switch are installed on the front face of the high-frequency power supply system 4, where the setting section 12 is used by the surgeon to set high-frequency power values to be supplied to the electrode section 3 and the display section 13 displays the set high-frequency power values and the like.

Figure 3:
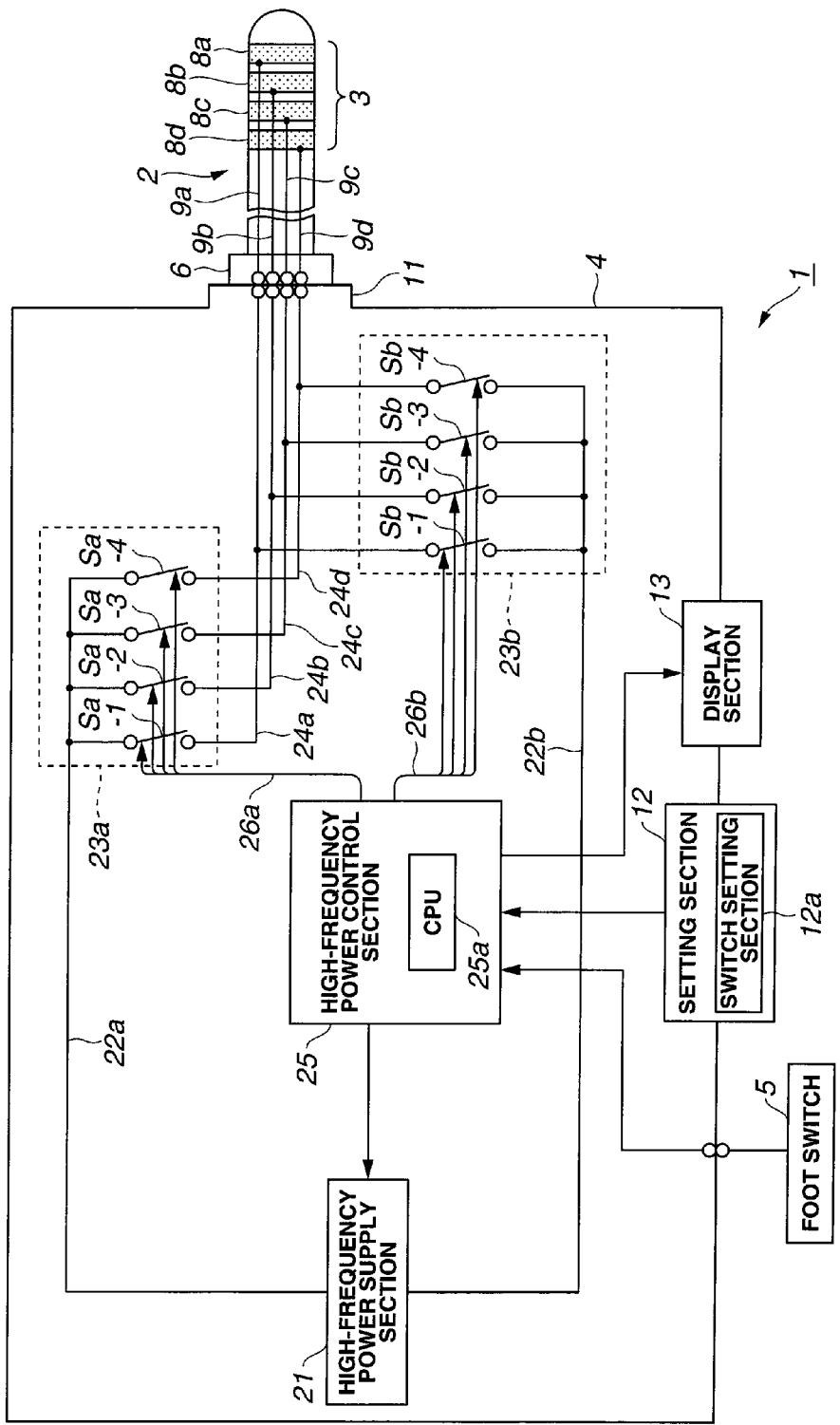

FIG. 3 shows an internal configuration of the high-frequency power supply system 4.

The high-frequency power supply system 4 includes a high-frequency power supply section 21 which outputs high-frequency power. Output terminals of the high-frequency power supply section 21 are connected, respectively, with switching sections 23a and 23b via high-frequency power supply lines (also referred to as power lines) 22a and 22b serving as signal lines used to supply high-frequency power.

The switching section 23a includes four switches Sa-1, Sa-2, Sa-3, and Sa-4. On the other hand, the switching section 23b includes four switches Sb-1, Sb-2, Sb-3, and Sb-4.

At one end, the switches Sa-j and Sb-j ($j$=1, 2, ..., 4) are connected to the output terminals of the high-frequency power supply section 21 via the power supply lines 22a and 22b. At the other end, the switches Sa-j as well as the switches Sb-j are connected, respectively, to four electrical contacts of the connector jack 11 via power lines 24*i*.

With the connector 6 connected to the connector jack 11, the electrodes 8*i* become electrically continuous with the switches Sa-j and Sb-j as follows.

Specifically, the electrode 8*a* becomes electrically continuous with the switches Sa-1 and Sb-1, the electrode 8*b* becomes electrically continuous with the switches Sa-2 and Sb-2, the electrode 8*c* becomes electrically continuous with the switches Sa-3 and Sb-3, and the electrode 8*d* becomes electrically continuous with the switches Sa-4 and Sb-4.

The high-frequency power supply system 4 includes a high-frequency power control section 25 which controls various parts of the high-frequency power supply system 4 and operation of the switching sections 23*a* and 23*b* and thereby controls high-frequency power output from the high-frequency power supply section 21. The high-frequency power control section 25 is configured by a built-in central processing unit (hereinafter referred to as a CPU) 25*a*.

The high-frequency power control section 25 controls operation of the switches Sa-j of the switching section 23*a* via a control line 26*a*, and operation of the switches Sb-j of the switching section 23*b* via a control line 26*b*.

The high-frequency power control section 25 is connected with the foot switch 5, the setting section 12 used to set high-frequency power values, and the display section 13.

In response to operation of the foot switch 5, the high-frequency power control section 25 controls ON and OFF of the high-frequency power output from the high-frequency power supply section 21. Also, the high-frequency power supply section 21 generates high-frequency power based on information on high-frequency power values inputted from the setting section 12 via the high-frequency power control section 25.

Also, the setting section 12 includes a switch setting section 12*a* which makes settings for the two sets of switches Sa-j and Sb-j (although "j" is used for the sake of simplicity, the two j's are not identical) to be turned on (closed) in the switching sections 23*a* and 23*b* as well as settings for switching times and the like. Based on information set by the switch setting section 12*a*, the high-frequency power control section 25 controls ON and OFF of the switches Sa-j and Sb-j via the control lines 26*a* and 26*b*.

As described later, according to the present embodiment, by turning on pairs of switches in sequence, the high-frequency power control section 25 supplies high-frequency power, in sequence, to pairs of adjacent electrodes out of multiple electrodes arranged along a longitudinal direction of the high-frequency probe 2.

That is, by changing the pair of electrodes used to supply high-frequency power in sequence, the present embodiment makes it possible to carry out a high-frequency procedure over a wide area of living tissue forming PFO at locations where the two electrodes contact.

Figure 4:
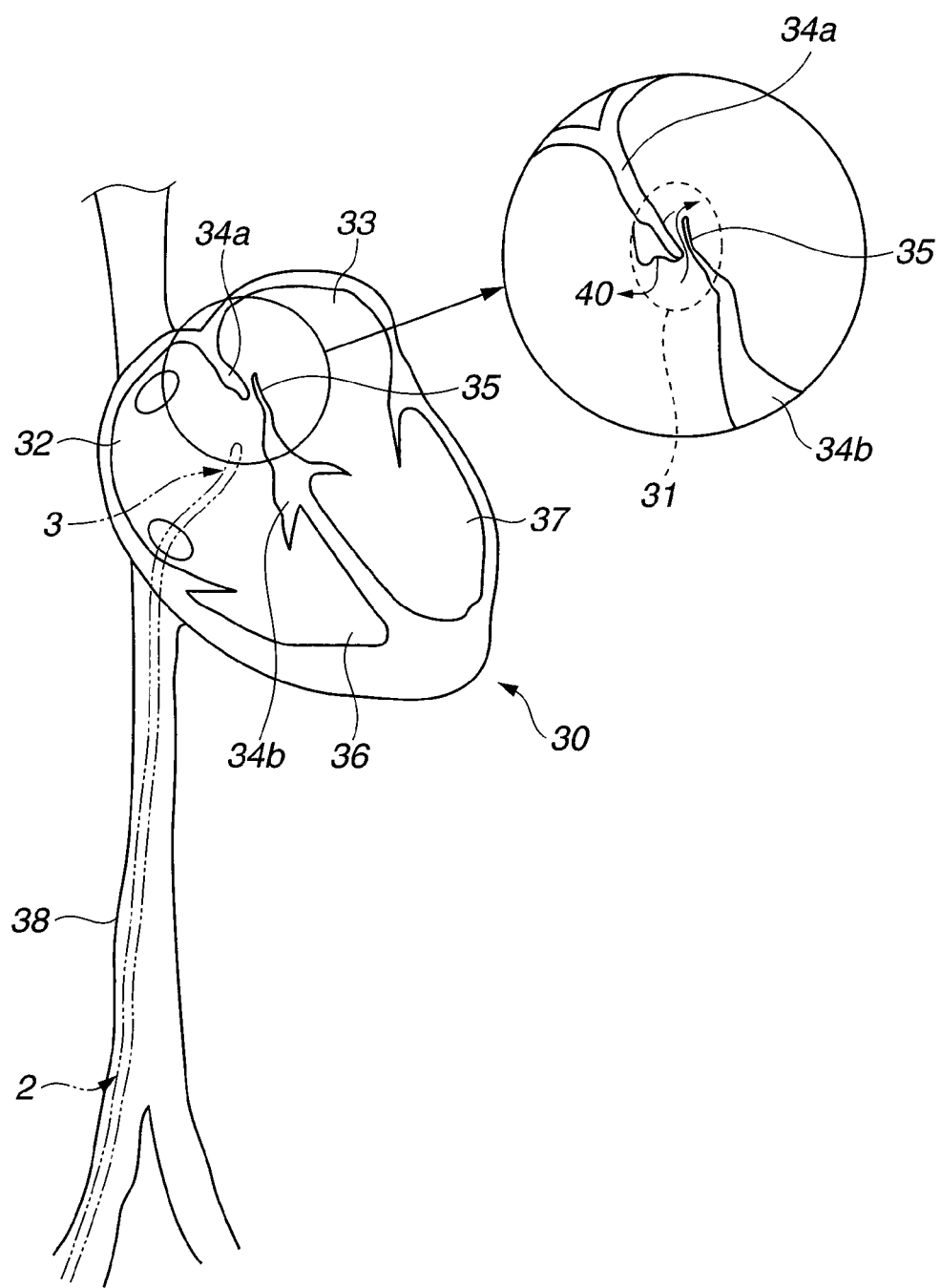

The high-frequency probe 2 shown in FIGS. 1 and 2 is inserted in PFO, as an object to be treated, in the heart shown in FIG. 4.

As shown in FIG. 4, the PFO 31 exists in part of the atrial septa 34*a* and 34*b* which separate the right atrium 32 from the left atrium 33 in the heart 30. The PFO 31 is equivalent to the condition in which valvula foraminis ovalis 35 remains separated from the atrial septum 34*a*. Blood flows around the PFO 31 as indicated by the arrows.

Besides, the right ventricle 36 and left ventricle 37 are located under the right atrium 32 and left atrium 33, respectively.

According to the present embodiment, when performing a treatment to close the PFO 31 using the high-frequency probe 2, the surgeon passes the high-frequency probe 2 through, for example, the inferior vena cava 38 communicating with the right atrium 32, as indicated by two-dot-chain lines.

Figure 5:
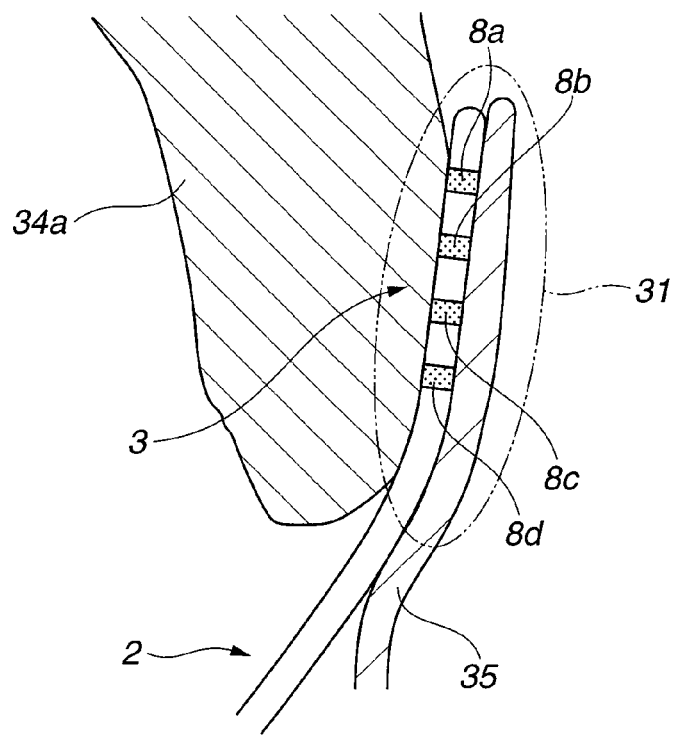
Figure 6:
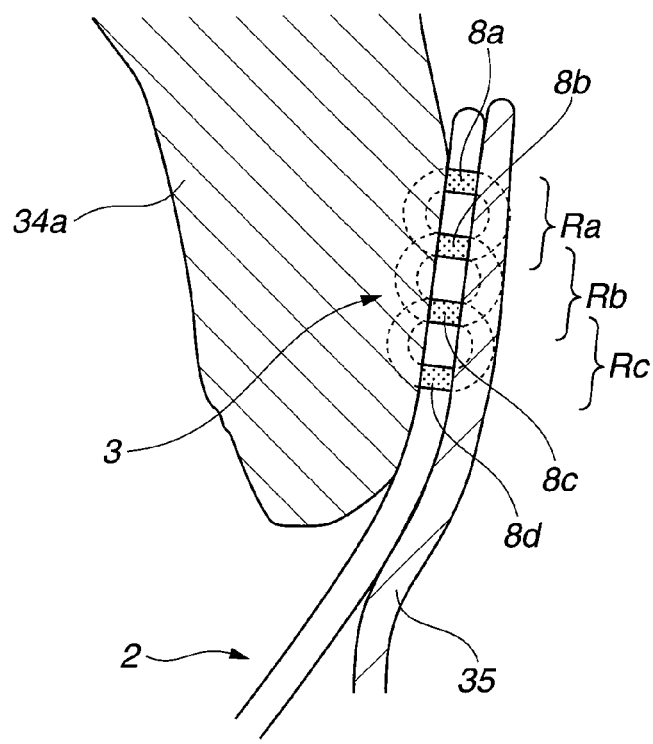

Furthermore, the surgeon inserts a distal side of the high-frequency probe 2 in the right atrium 32 through an orifice communicating with the right atrium 32, sets the distal side of the high-frequency probe 2 in the PFO 31 as shown in FIG. 5, and thereafter carries out a high-frequency procedure as shown in FIG. 6.

Thus, the high-frequency probe 2 has an elongated structure small enough in outside diameter to allow the high-frequency probe 2 to be passed through a blood vessel, namely, the inferior vena cava 38 and long enough for the distal end to be placed in the PFO 31 by passing through the blood vessel. A catheter 41 described later also has an elongated structure.

Next, procedures of the treatment for closing the PFO 31 using the high-frequency surgical apparatus 1 according to the present embodiment will be described with reference to FIG. 7.

First, the surgeon sets up the high-frequency surgical apparatus 1 as shown in FIG. 1. Then, the surgeon turns on the high-frequency power supply system 4. Consequently, the high-frequency power supply system 4 is activated.

As shown in Step S1, the surgeon makes initial settings: sets the high-frequency power value, sets the time for which high-frequency power will be supplied to the two electrodes used for the treatment out of the electrodes 8*a* to 8*d*, and so on. According to the present embodiment, using the setting section 12, the surgeon can also specify the order in which pairs of electrodes used for the treatment will be selected. In the following example, description will be made assuming that pairs of electrodes are selected in sequence, beginning at the distal side and going to the proximal side.

Next, in Step S2, the surgeon inserts the high-frequency probe 2 into a blood vessel of the patient. For example, the surgeon inserts the high-frequency probe 2 into the inferior vena cava 38 of the patient as shown in FIG. 4.

Next, in Step S3, the surgeon inserts the distal end of the high-frequency probe 2 into the right atrium 32 of the heart 30 and positions or sets the electrode section 3 at the distal end in the PFO 31 in the inner part of the right atrium 32.

As shown in FIG. 5, the surgeon places the electrodes 8*a*, 8*b*, 8*c*, and 8*d* of the electrode section 3 between the atrial septum 34*a* and valvula foraminis ovalis 35 which are living tissues forming the PFO 31, where the electrode section 3 serves as a treatment section (used for the treatment), being located at the distal end of the high-frequency probe 2. Incidentally, blood is flowing around the PFO 31.

After the positioning, the surgeon depresses (turns on) the foot switch 5 as shown in Step S4.

Consequently, based on the initial settings, the high-frequency power control section 25 outputs high-frequency power to the electrode section 3 from the high-frequency power supply section 21 via the switching sections 23*a* and 23*b*.

In this case, as shown in Step S5, the high-frequency power control section 25 turns on the switches Sa-1 and Sb-2 to supply high-frequency power to the electrodes 8*a* and 8*b*. Incidentally, all the switches other than the switches Sa-1 and Sb-2 remain off (opened).

Consequently, with the electrode section 3 positioned as shown in FIG. 5, a high-frequency current flows, for example, as indicated by dotted lines, through the part of the atrial septum 34*a* and valvula foraminis ovalis 35 (indicated by Ra)

which is located in the vicinity between the electrodes 8a and 8b, as shown in FIG. 6. As a result, the part of the atrial septum 34a and valvula foraminis ovalis 35 which is indicated by Ra is heated by the high-frequency power and damaged by the high-frequency cauterization procedure.

As shown in Step S6, the high-frequency power control section 25 waits for a predetermined period of time, for example, by starting a timer when the high-frequency power starts to be supplied. When the predetermined period of time elapses, the high-frequency power control section 25 turns on the switches Sa-2 and Sb-3 to supply high-frequency power to the electrodes 8b and 8c as shown in Step S7. That is, the high-frequency power control section 25 also controls the duration of the high-frequency cauterization procedure.

When the switches Sa-2 and Sb-3 are turned on, a high-frequency current flows, for example, as indicated by dotted lines, through the part of the atrial septum 34a and valvula foraminis ovalis 35 which is located in the vicinity between the electrodes 8b and 8c and indicated by Rb. As a result, the part of the atrial septum 34a and valvula foraminis ovalis 35 which is indicated, for example, by Rb is heated by the high-frequency power and damaged by the high-frequency cauterization procedure.

As shown in Step S8, the high-frequency power control section 25 waits for a predetermined period of time after the high-frequency power starts to be supplied. When the predetermined period of time elapses, the high-frequency power control section 25 turns on the switches Sa-3 and Sb-4 to supply high-frequency power to the electrodes 8c and 8d as shown in Step S9.

In this case, a high-frequency current flows, for example, as indicated by dotted lines, through the part of the atrial septum 34a and valvula foraminis ovalis 35 which is located in the vicinity between the electrodes 8c and 8d and indicated by Rc, causing damage by the high-frequency cauterization procedure.

Also, as shown in Step S10, the high-frequency power control section 25 waits for a predetermined period of time after the high-frequency power starts to be supplied. When the predetermined period of time elapses, the high-frequency power control section 25 displays a message, for example, on the display section 13, indicating that the high-frequency procedure has been finished.

When there are four electrodes, three pairs of electrodes are selected. When the number of electrodes is N, "N–1" pairs of electrodes are selected in sequence.

According to the message, the surgeon turns off the foot switch 5 as shown in Step ST11. Then, as shown in Step S12, the surgeon removes the high-frequency probe from the blood vessel, and thereby finishes the procedure for closing the PFO 31.

As described above, the living tissue of the PFO 31 is damaged by heat with the application of high-frequency power. After the procedure, the damaged living tissue heals. During healing, the atrial septum 34a and valvula foraminis ovalis 35, which are pressed against each other in their natural state, fuse together and close naturally by themselves. This completes closure of the PFO 31.

As described above, according to the present embodiment, at the distal end of the high-frequency probe 2, three or more electrodes 8a to 8d are installed along the longitudinal direction, making it possible to treat a wider area of living tissue of the PFO 31 with high-frequency power than when only two electrodes are used.

According to the present embodiment, pairs of electrodes are selected in sequence from the three or more electrodes 8a to 8d installed along the longitudinal direction of the high-frequency probe 2. Consequently, a high-frequency current flows through the living tissue of the PFO 31, making it possible to cauterize a wide area of the living tissue along the longitudinal direction of the high-frequency probe 2, and thereby close a wide area of the PFO 31 along the longitudinal direction.

In this way, the present embodiment can enhance the capability to close the PFO 31.

Second Embodiment

A second embodiment of the present invention will be described below with reference to FIGS. 8 to 13. The present embodiment is intended to facilitate the high-frequency cauterization procedure by bringing the high-frequency probe 2 equipped with the electrode section 3 into close contact or pressing contact with the living tissues of the PFO 31.

For this end, the present embodiment includes not only the high-frequency probe 2, but also a pressing mechanism as an auxiliary member used to bring the electrode section 3 at the distal end of the high-frequency probe 2 into close contact with the PFO 31.

Figure 8:
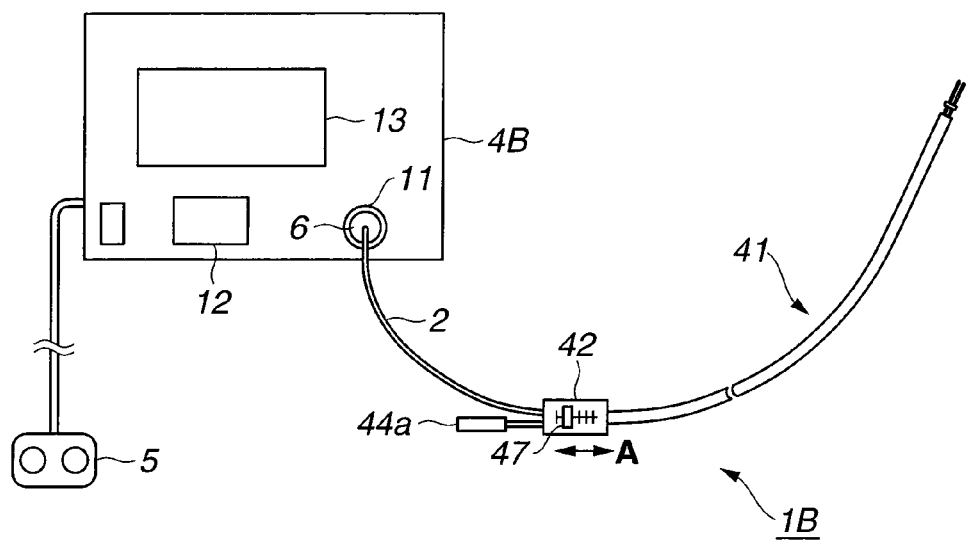
FIGS. 8 to 13 relate to a second embodiment of the present invention, where.

FIG. 8 shows a high-frequency surgical apparatus 1B according to the second embodiment of the present invention.

The high-frequency surgical apparatus 1B includes a catheter 41 which allows passage of the high-frequency probe 2, and a high-frequency power supply system 4B detachably connected with a connector 6 at the proximal end of the high-frequency probe 2 extending from a grasping section 42 at a proximal end of the catheter 41.

Figure 9:
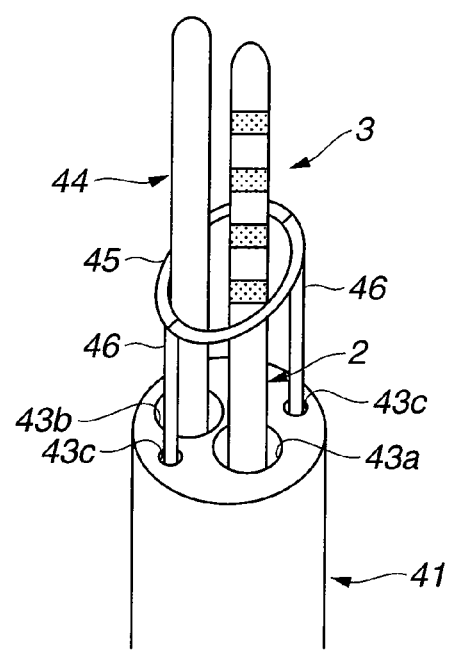

As shown in FIG. 9, the catheter 41 has a lumen 43a through which the high-frequency probe 2 is passed, a lumen 43b through which a probe 44 used for pressing is passed, and lumens 43c through which stems 46 of a ring-shaped member 45 are passed.

The catheter 41 also has such outside diameter and length insertable into the blood vessel leading to the PFO 31.

The distal end of the high-frequency probe 2 which protrudes from a distal end face of the catheter 41 and distal end of the probe 44 are passed through the annular, ring-shaped member 45. That is, the ring-shaped member 45 functions as a restricting member which restricts distance between the distal side of the high-frequency probe 2 and distal side of the probe 44 to within an inside diameter of the ring. Also, the lumens 43a and 43b are installed in such a way as to be located within the inside diameter of the ring-shaped member 45.

The ring-shaped member 45 is installed at a distal end of, for example, two stems 46, or alternatively may be installed at a distal end of one stem. Outside diameter of the ring-shaped member 45 is smaller than outside diameter of the catheter 41.

At the rear end, the stems 46 are linked to a slide lever 47, which is slidable, in the grasping section 42 shown in FIG. 8. The slide lever 47 is movable along a longitudinal direction (indicated by A) of the catheter 41. By moving the slide lever 47, the surgeon can change an amount of protrusion of the ring-shaped member 45 from the distal end face of the catheter 41 along the longitudinal direction.

A proximal side of the probe 44 passed through the lumen 43b in the catheter 41 extends rearward from the grasping section 42. A slidable grasping section 44a to be grasped and slidably operated by the surgeon is attached to a proximal end of the probe 44.

Figure 10:
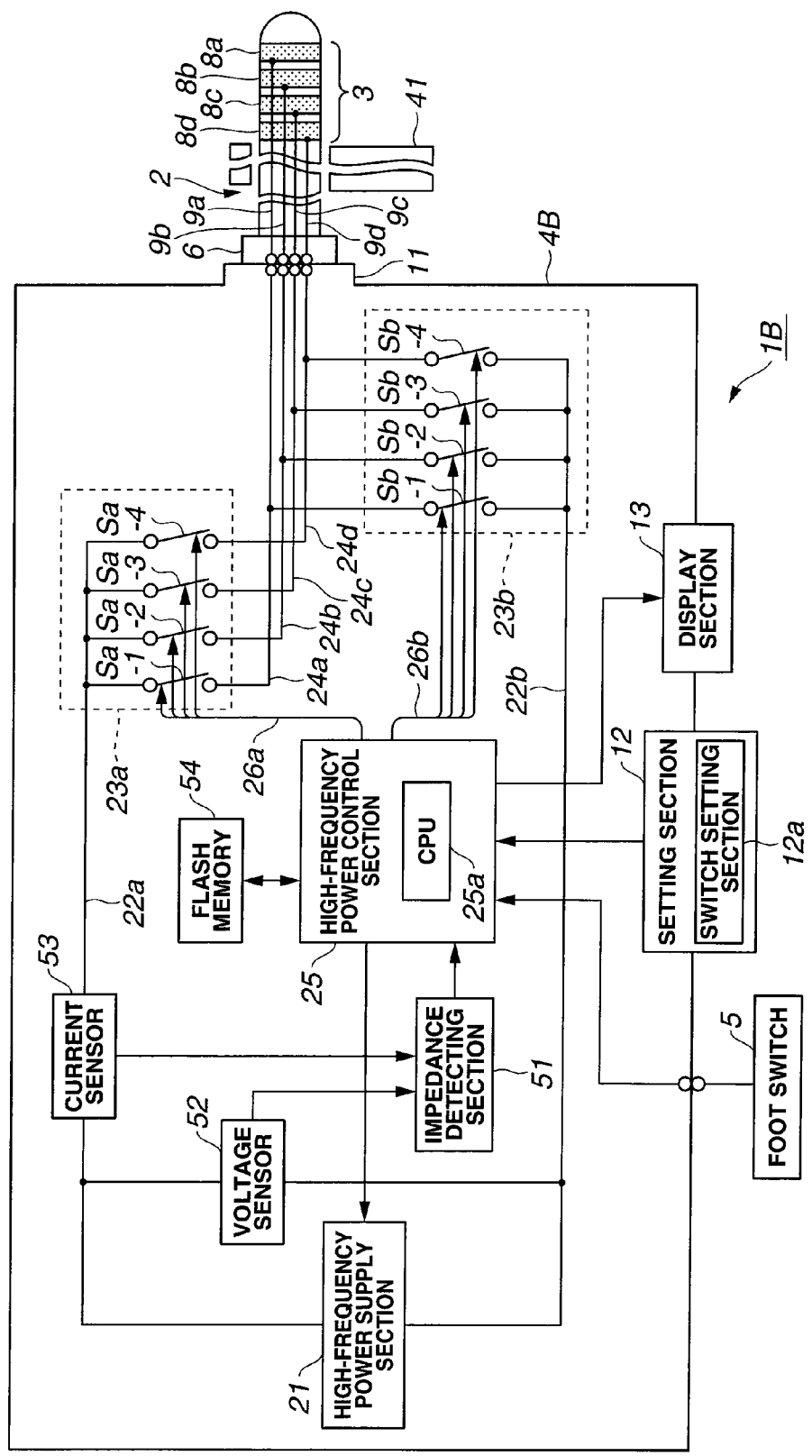

The high-frequency power supply system 4B according to the present embodiment is configured as shown in FIG. 10. Compared, for example, to the high-frequency power supply system 4 shown in FIG. 3, the high-frequency power supply system 4B further includes an impedance detecting section 51.

A voltage sensor 52 and current sensor 53 are installed on the output terminals of the high-frequency power supply section 21 to detect high-frequency voltage and high-frequency current, respectively. Voltage and current values detected by the voltage sensor 52 and current sensor 53 are inputted in the impedance detecting section 51.

The impedance detecting section 51 detects an impedance value and output the impedance value to the high-frequency power control section 25.

Based on the detected impedance value, the high-frequency power control section 25 determines, with reference to information stored in a flash memory 54, whether or not impedance of the two electrodes is close to a standard impedance value which corresponds to a condition in which two electrodes are placed in relation to the living tissue of the PFO 31 as intended by the surgeon.

The flash memory 54 serving as an information storage section prestores information about the standard impedance value corresponding to a condition, for example, shown in FIG. 5 in which two electrodes are placed in proper contact with the living tissue of the PFO 31.

Blood flows around the PFO 31, and the atrial septum 34a and valvula foraminis ovalis 35, i.e., the living tissue of the PFO 31, have a higher impedance value than the blood. Consequently, when the distal side of the high-frequency probe 2 is set in proper condition as shown in FIG. 5, an impedance value of the distal side is equal to or higher than a predetermined threshold. Thus, information as to whether or not the detected impedance value is equal to or higher than the predetermined threshold provides a measure of whether or not the distal end of the high-frequency probe 2 is set in a condition suitable for the treatment.

Incidentally, the flash memory 54 may also store information about a rate of change of the standard impedance value before and after the high-frequency cauterization of the PFO 31.

Also, the high-frequency power control section 25 displays, in the display section 13, a result of determination as to whether or not the detected impedance value is in an acceptable predetermined range.

The determination result displayed in the display section 13 makes it easier for the surgeon to check whether the electrode section 3 at the distal end of the high-frequency probe 2 is in a condition suitable for treating the living tissue of the PFO 31.

Figure 11:
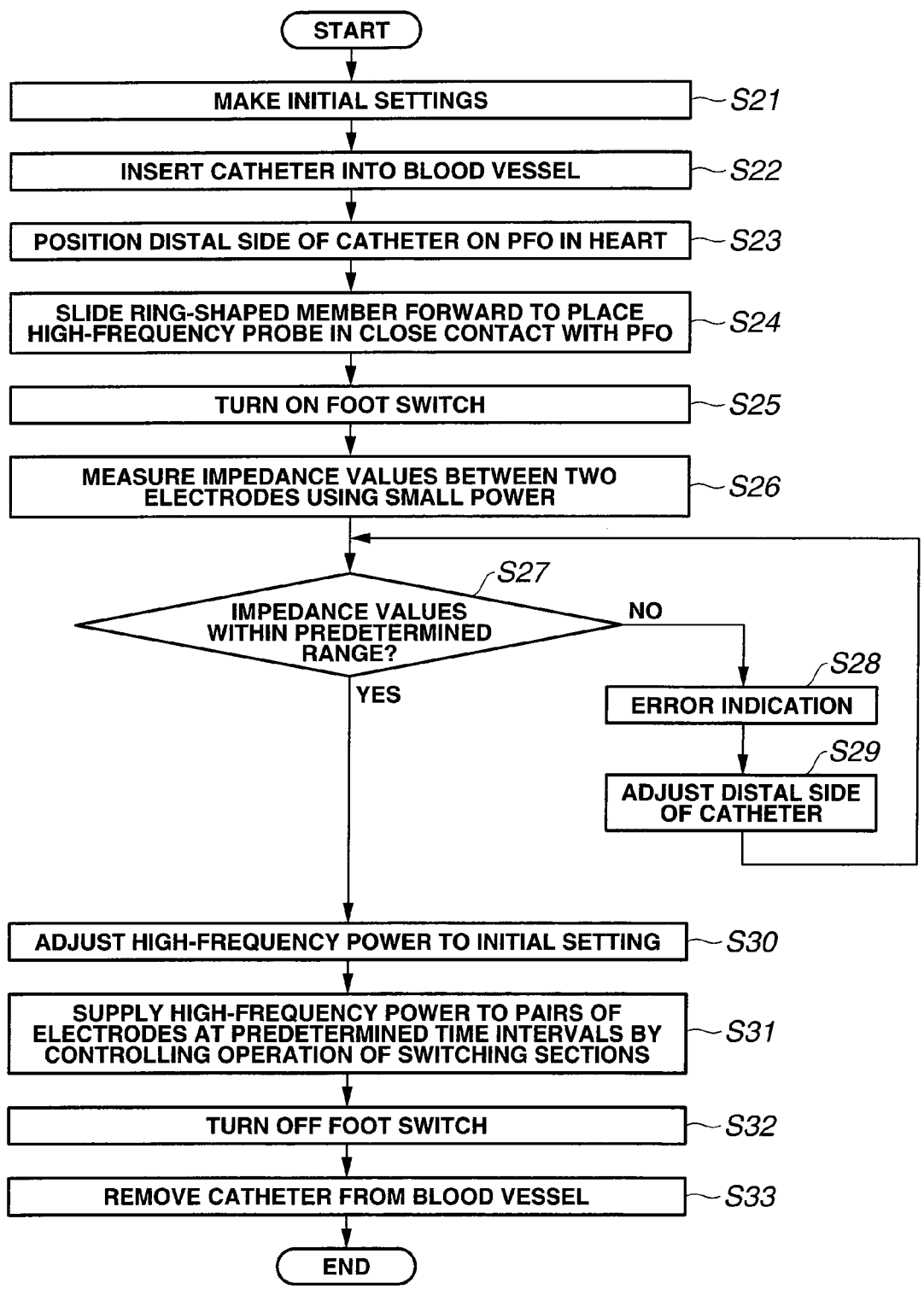

Next, procedures for high-frequency surgery according to the present embodiment will be described below with reference to FIG. 11. The procedures are similar to those in FIG. 7.

First, the surgeon sets up the high-frequency surgical apparatus 1B as shown in FIG. 8. Then, the surgeon turns on the high-frequency power supply system 4B. Consequently, the high-frequency power supply system 4B is activated.

Figure 7:
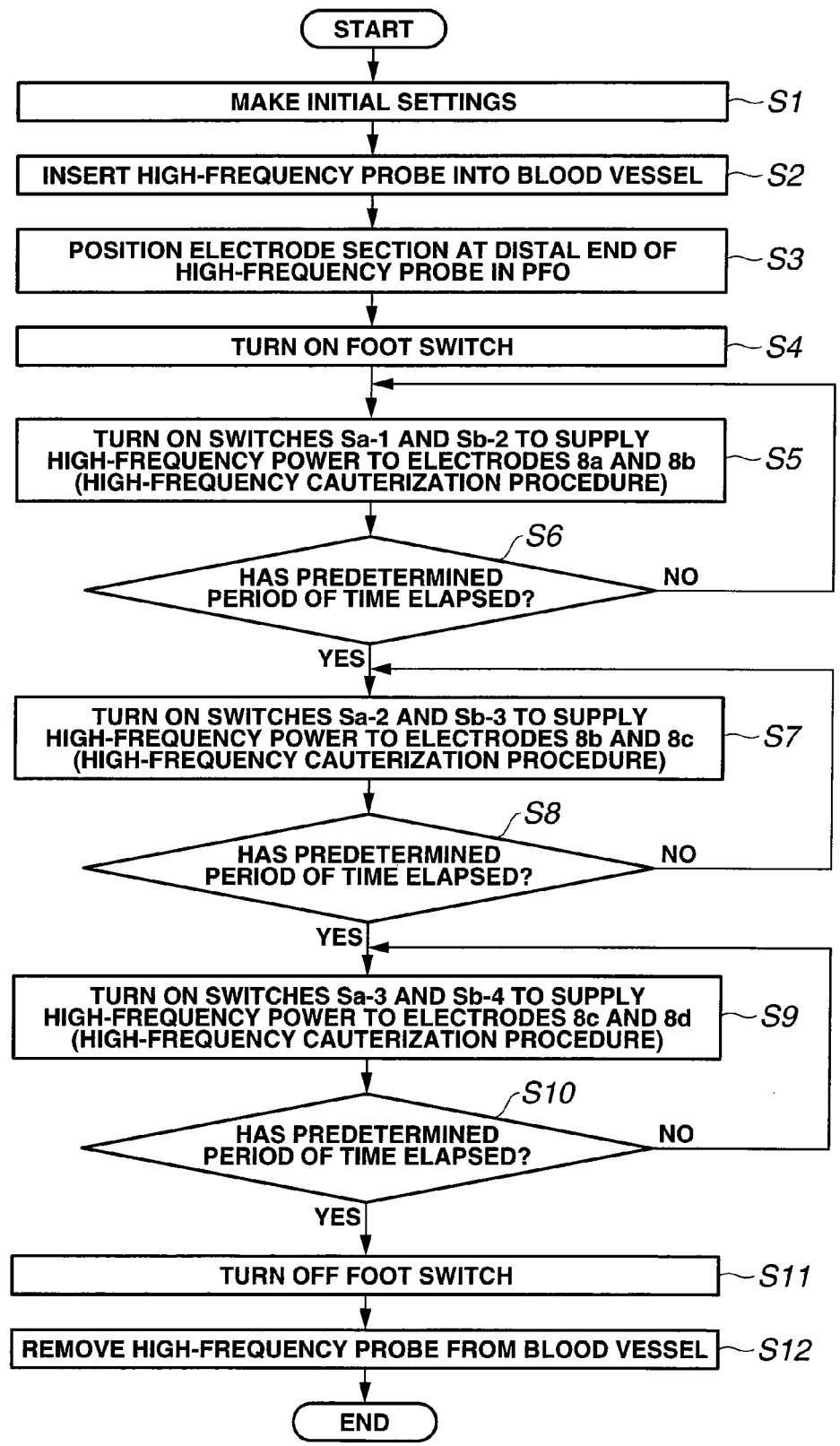

As shown in Step S21, the surgeon makes initial settings, as in the case of Step S1 in FIG. 7.

Next, in Step S22, the surgeon inserts the catheter 41 into a blood vessel of the patient, the catheter 41 including the high-frequency probe 2, the probe 44, and the ring-shaped member 45. The surgeon inserts the catheter 41 into the blood vessel of the inferior vena cava 38 of the patient instead of the high-frequency probe 2, for example, in a manner shown in FIG. 4. In this case, the ring-shaped member 45 is placed in such a position as to contact the distal end face of the catheter 41.

Next, in Step S23, the surgeon inserts the catheter 41 into the right atrium 32 of the heart 30 and positions the distal side of the catheter 41 on the PFO 31 in the inner part of the right atrium 32.

Specifically, after placing the distal side of the catheter 41 in front of the PFO 31, the surgeon protrudes the high-frequency probe 2 from inside of the catheter 41, inserts the high-frequency probe 2 into the PFO 31, and positions the high-frequency probe 2. The positioning is done in the same manner as in the first embodiment, and the distal end of the high-frequency probe 2 is positioned in the PFO 31 between the atrial septum 34a and valvula foraminis ovalis 35.

Then, the surgeon protrudes the probe 44 out of the distal end face of the catheter 41 and places the probe 44 in such a way as to sandwich the atrial septum 34a between the probe 44 and the high-frequency probe 2 from outside the PFO 31 (opposite side of the atrial septum 34a).

In other words, the surgeon positions the probe 44 nearer to the right atrium 32 on the face of the atrial septum 34a, the face being the opposite of the face on which the high-frequency probe 21 is positioned.

After the distal side of the catheter 41 is positioned on the PFO 31 in this way, while sliding the ring-shaped member 45 to the front (far side) of the distal end face of the catheter 41, the surgeon presses the probe 44 outside the PFO 31 against the atrial septum 34a by manipulating the catheter 41, as shown in Step S24.

By sliding the ring-shaped member 45, the surgeon can limit flexing part of the probe 44 outside the PFO 31 (only the part farther than the ring-shaped member will flex).

That is, by moving the ring-shaped member 45 farther, the surgeon can increase the amount of force by which to press the atrial septum 34a against the PFO 31 using the probe 44 placed outside the PFO 31. This makes it easier to place the distal end of the high-frequency probe 2 into close contact or pressing contact with the living tissue of the PFO 31.

Figure 12:
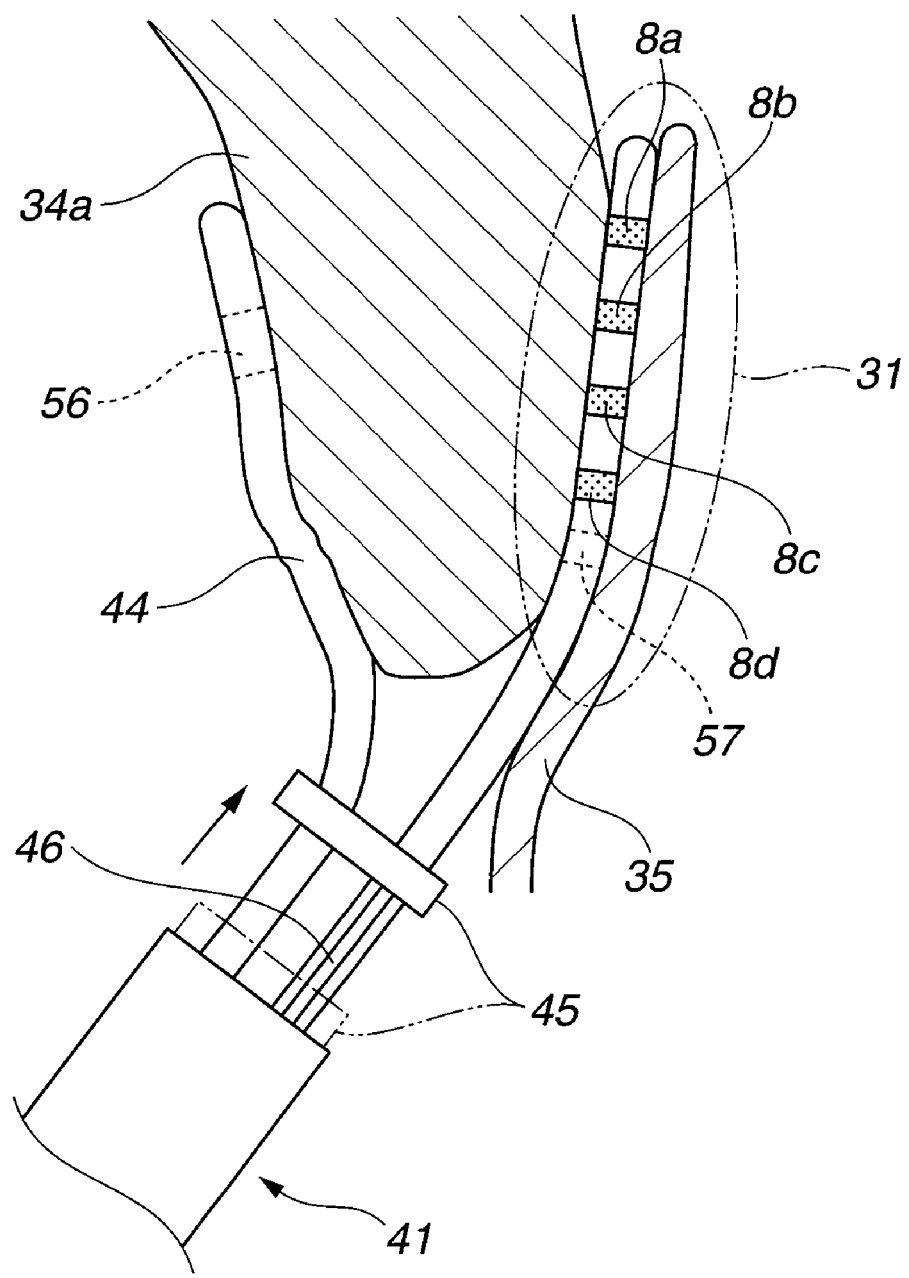

FIG. 12 shows a state where the distal side of the high-frequency probe 2 and probe 44 is placed in close contact with the living tissue of the PFO 31. In this case, the ring-shaped member 45 indicated by a two-dot-chain line is moved forward as indicated by solid lines to make it easier to place the high-frequency probe 2 into close contact or pressing contact with the living tissue of the PFO 31.

Next, as shown in Step S25, the surgeon turns on the foot switch 5.

Then, as shown in Step S26, the high-frequency power control section 25 detects or measures the impedance values between two electrodes using small power. For example, the high-frequency power control section 25 detects the impedance value between each pair of electrodes: 8a and 8b, 8b and 8c, and 8c and 8d. Alternatively, the impedance value may be detected only between a single pair of electrodes, for example, between electrodes 8a and 8b.

Next, in Step S27, the high-frequency power control section 25 determines whether the impedance values fall within an acceptable predetermined range. The detected impedance values may be displayed in the display section 13.

If the detected impedance values are not within the predetermined range, the high-frequency power control section 25 makes the display section 13 provide an error indication in Step S28. The display section 13 displays a message, informing the surgeon that the detected impedance values are not within the acceptable predetermined range. Incidentally, the error indication is not limited to a visual form, and may be in the form of voice or the like.

When the detected impedance values are not within the predetermined range, the surgeon adjusts the distal side of the catheter 41, for example, as shown in Step S29. Then, the flow returns to Step S27.

If it is found in Step S27 that the impedance values fall within the acceptable predetermined range, the high-frequency power control section 25 sets the high-frequency power value to the initially set value, as shown in Step S30.

Next, as shown in Step S31, the high-frequency power control section 25 controls operation of the switching sections 23*a* and 23*b* so that high-frequency power will be supplied to pairs of electrodes in the electrode section 3 at predetermined time intervals. Step S31 corresponds to Steps S5 to S10 in FIG. 7.

When the high-frequency cauterization procedure is finished using all the three pairs of electrodes, the surgeon turns off the foot switch 5 in Step S32. Furthermore, as shown in Step S33, the surgeon removes the catheter 41 from the blood vessel, and thereby finishes the procedure for closing the PFO 31.

Being equipped with a mechanism for placing the high-frequency probe 2 into close contact with the PFO 31, the present embodiment provides the advantage of improving capabilities of high-frequency cauterization procedure for the PFO 31 in addition to the same advantages as the first embodiment. Incidentally, the probe 44 is not limited to one without an electrode section, and may be the same type as, for example, the high-frequency probe 2.

In that case, the surgeon may position one of the two high-frequency probes in the PFO 31 and use the other one as an auxiliary probe to be placed in close contact with the PFO 31.

As a variation of the present embodiment, for example, as indicated by a dotted line in FIG. 12, a pressure sensor 56 may be installed on an outer periphery on the distal side of the probe 44. In this case, a detection signal from the pressure sensor 56 is inputted in the high-frequency power control section 25 of the high-frequency power supply system 4B via a signal line in the probe 44.

Also, the high-frequency power control section 25 may determine whether a pressure value detected by the pressure sensor 56 is appropriate and display a determination result in the display section 13.

The detected pressure value may also be displayed in the display section 13. Again, based on the determination result and detected pressure value, the surgeon can determine whether the high-frequency probe 2 and probe 44 sticking out from the distal end face of the catheter 41 are in a condition suitable for the treatment.

Figure 13:
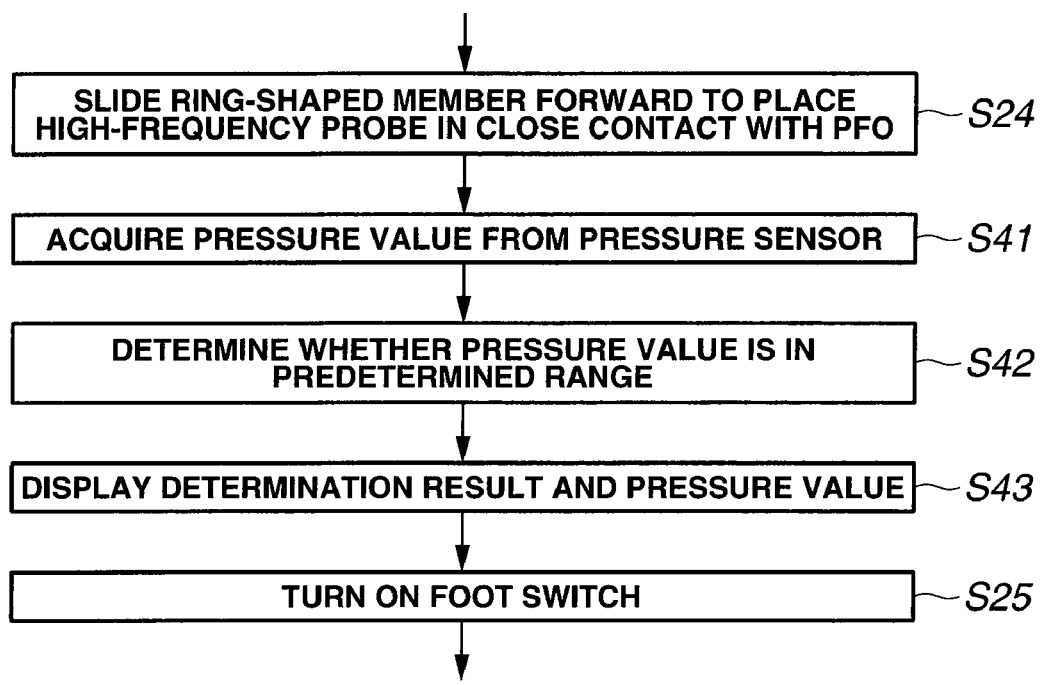

Operation performed in this case is shown in FIG. 13. Specifically, the following steps are carried out between Steps S24 and S25 in FIG. 1.

In Step S41 after Step S24, the high-frequency power control section 25 acquires a pressure value detected by the pressure sensor 56. Next, in Step S42, the high-frequency power control section 25 determines whether the acquired pressure value is in a predetermined pressure range corresponding to settings suitable for the treatment. Next, in Step S43, the high-frequency power control section 25 displays a result of the determination and the pressure value in the display section 13.

By referring to the determination result, the surgeon can check condition of the distal side of the catheter 41. If the surgeon learns that the pressure value is too small, the surgeon adjusts the distal side of the catheter 41. Then, the flow goes to Step S25 and subsequent steps in FIG. 11.

The present variation also makes it possible to check the condition of the distal side of the catheter 41, and thereby makes it easier to carry out the high-frequency cauterization procedure at appropriate settings.

Also, as indicated by dotted lines in FIG. 12, a pressure sensor 57 may be installed, for example, next to the electrode 8*d* on an outer periphery of the high-frequency probe 2. This makes it possible to implement the same functions as the pressure sensor 56. Besides, since the pressure sensor 57 is installed on the high-frequency probe 2, this configuration can also be applied to the first embodiment.

Steps S41 to S43 in FIG. 13 may be carried out, for example, between Steps S3 and S4 in FIG. 7. This will make it easier to see whether or not the high-frequency probe 2 is positioned in an acceptable manner just before a high-frequency procedure in the first embodiment.

Third Embodiment

A third embodiment of the present invention will be described below with reference to FIGS. 14 to 19. The present embodiment involves placing the high-frequency probe outside the PFO 31 (outside the valvula foraminis ovalis 35) instead of inserting the high-frequency probe in the PFO 31. Then, the PFO 31 is cauterized inward from outside the valvula foraminis ovalis 35.

Also, the present embodiment improves therapeutic effects by cauterizing the PFO 31 using high-frequency power while pressing the PFO 31 from outside in such a way as to produce effects similar to the second embodiment.

Figure 14:
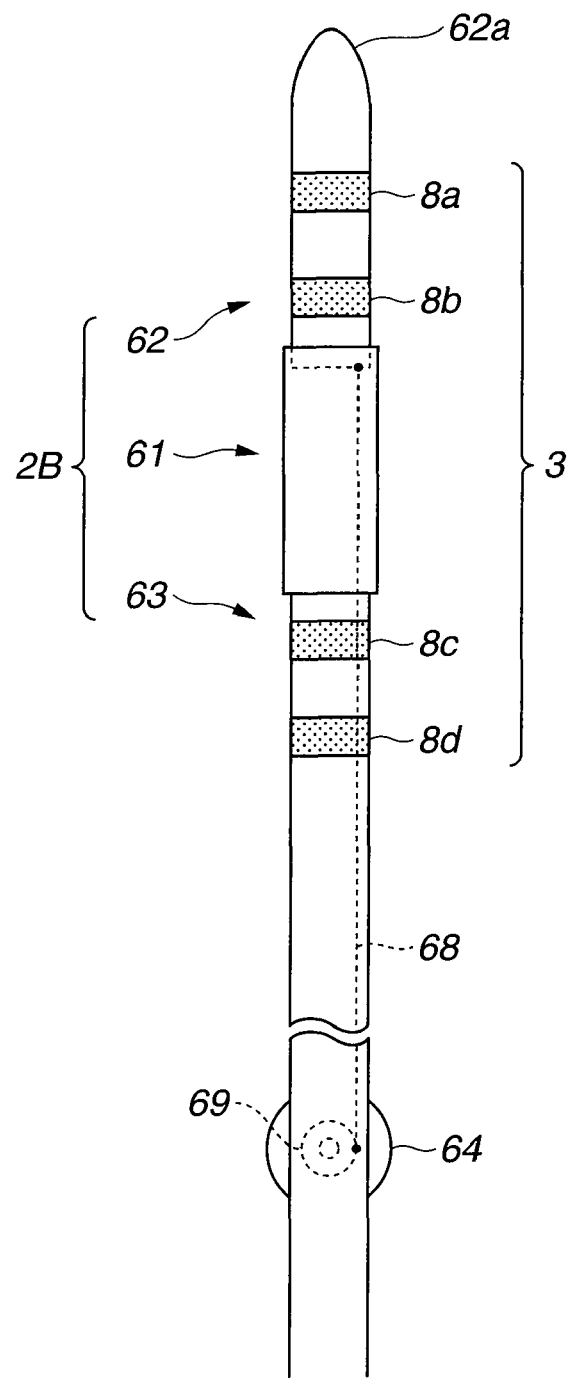
FIGS. 14 to 19 relate to a third embodiment of the present invention, where.

FIG. 14 shows a configuration of the distal side of a high-frequency probe 2B according to the third embodiment of the present invention.

Basically, the high-frequency probe 2B has an electrode section 3 which includes three or more electrodes 8*a* to 8*d*, as in the case of the first embodiment. Furthermore, a flexing section 61 flexible, for example, in a single direction is installed near the electrode section 3.

The high-frequency probe 2B shown in FIG. 14 is configured such that the flexing section 61 is installed, for example, between two parts of the high-frequency probe 2, separating the part (referred to as a distal probe member 62) in which the two electrodes 8*a* and 8*b* are installed from the part (referred to as a probe body 63) in which the two electrodes 8*c* and 8*d* are installed, the part being located behind the first part.

That is, the high-frequency probe 2B includes the distal probe member 62 in which the two electrodes 8*a* and 8*b* are installed, the probe body 63in which the two electrodes 8*c* and 8*d* are installed, and the flexing section 61 installed between the distal probe member 62 and probe body 63.

Also, an operation knob 64 is installed on a proximal side of the high-frequency probe 2B to allow the surgeon to flex the flexing section 61.

Figure 15:
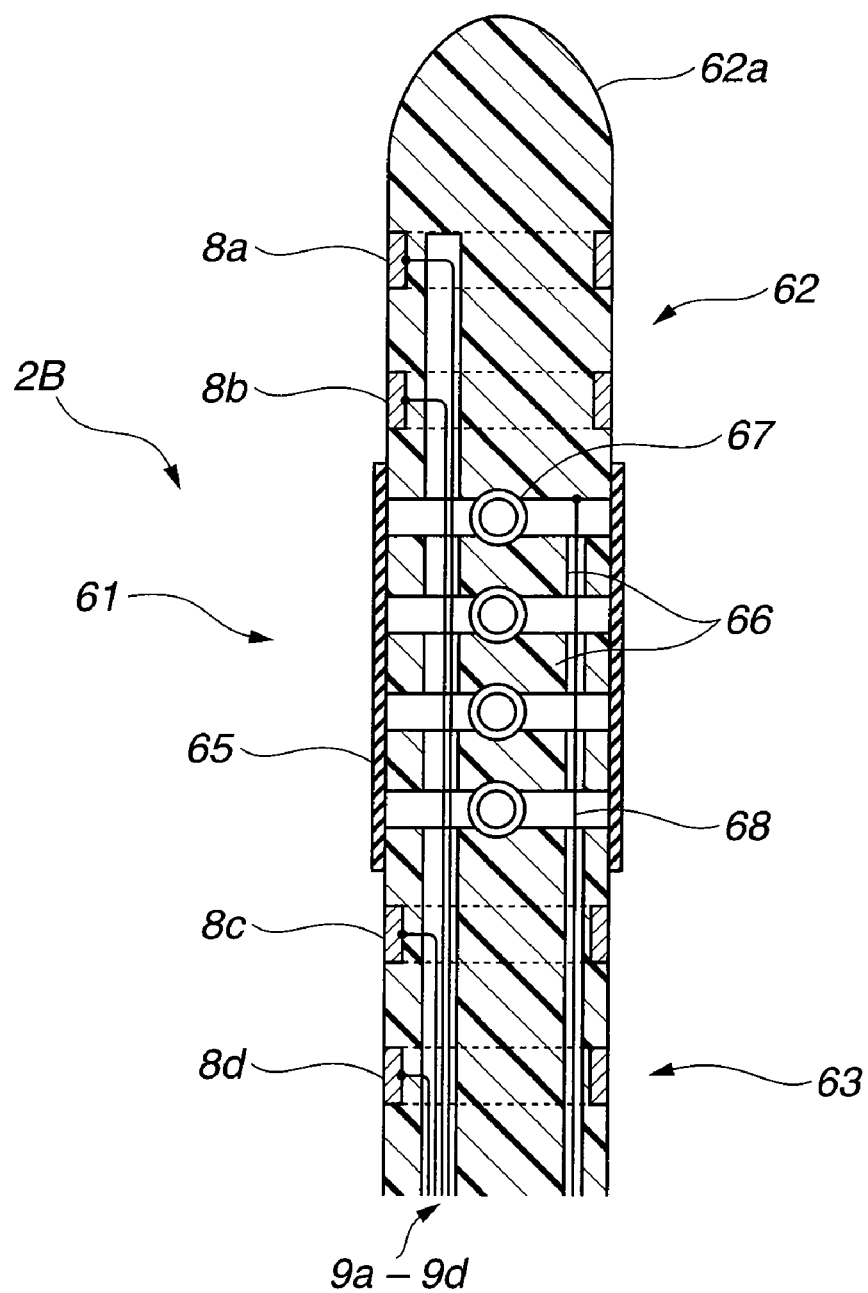
Figure 16:
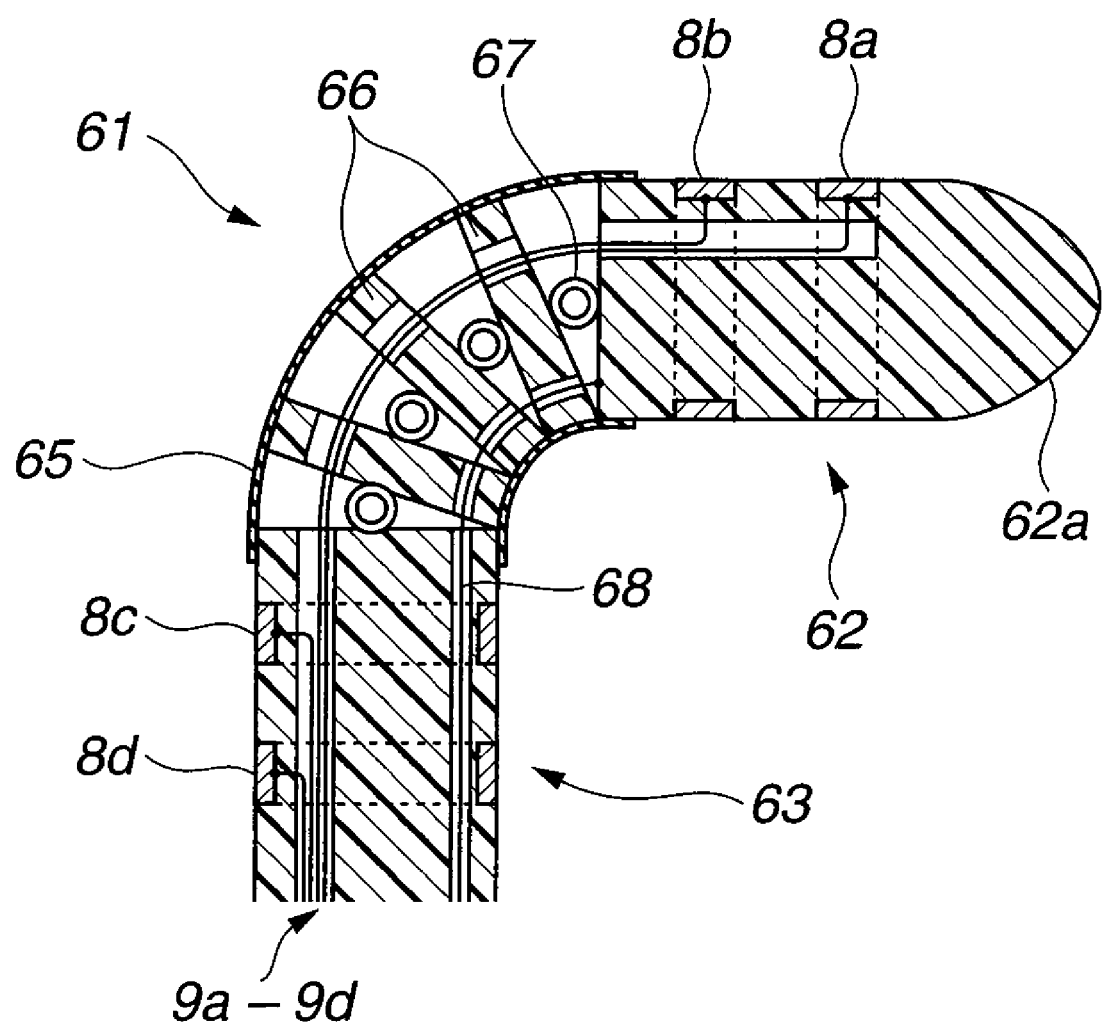

FIG. 15 shows a structure of the flexing section 61 and its surroundings. FIG. 16 shows the flexing section 61 as the flexing section 61 is flexed. The flexing section 61 includes multiple joint members 66 coupled rotatably in an elastic, cylindrical, rubber cover 65 along a longitudinal direction of the high-frequency probe 2B.

The joint members 66 are, for example, solid, ring-shaped (disk-shaped) members and rivets 67 are used to rotatably couple adjacent joint members. The rivets 67 are installed in pairs with the rivets in each pair facing each other in the direction perpendicular to the plane of the paper in FIG. 15.

The most distal joint member 66 is coupled with a rear end (proximal end) of the distal probe member 62 by means of rivets 67. The rearmost joint member 66 is coupled to a distal end of the probe body 63 by means of rivets 67.

A distal end of a flexion control wire (hereinafter referred to simply as a wire) 68 is fastened to the distal probe member 62 at a position spaced from rivets 67 used for rotatable coupling. Although a single wire 68 is used here, by installing a wire also on the opposite side, the flexing section 61 may be flexed not only rightward in FIG. 15, but also leftward.

A guide hole is formed in each joint member 66 in order for the wire 68 to pass thorough. The wire 68 passed thorough the guide holes is passed thorough a lumen installed along a longitudinal direction of the probe body 63.

Also, lead wires 9a and 9b whose distal ends are fixed to the electrodes 8a and 8b are passed through guide holes formed in the joint members 66, and then through a lumen installed along the longitudinal direction of the probe body 63. Also, lead wires 9c and 9d are passed through the lumen.

Incidentally, the joint members 66 may be configured as hollow ring-shaped members. In this case, there is no need for guide holes.

A proximal end of the wire 68 is fixed to a pulley 69 coupled to the operation knob 64 shown in FIG. 14.

The pulley 69 has a rotatable central axis coupled to the operation knob 64. By rotating the operation knob 64, the surgeon hauls the wire 68 fixed to an outer periphery of the pulley 69 toward the proximal side of the high-frequency probe 2, i.e., toward the pulley 69. The hauled wire 68 causes the flexing section 61 to flex as shown in FIG. 16.

In the high-frequency probe 2B according to the present embodiment, the distal probe member 62 has a pointed distal end section 62a. With the pointed distal end section 62a pressed against the atrial septum 34a, the surgeon can stick the distal end section 62a into the atrial septum 34a by applying a pushing force and cause a distal side of the high-frequency probe 2B to penetrate the atrial septum 34a by further applying a pushing force.

With the high-frequency probe 2B configured as described above, procedures for closing the PFO 31 by high-frequency cauterization with the high-frequency probe 2B will be described with reference to FIG. 17, assuming the use of, for example, the high-frequency power supply system 4 in FIG. 3. However, the high-frequency power supply system 4B in FIG. 10 may be used alternatively.

Figure 17:
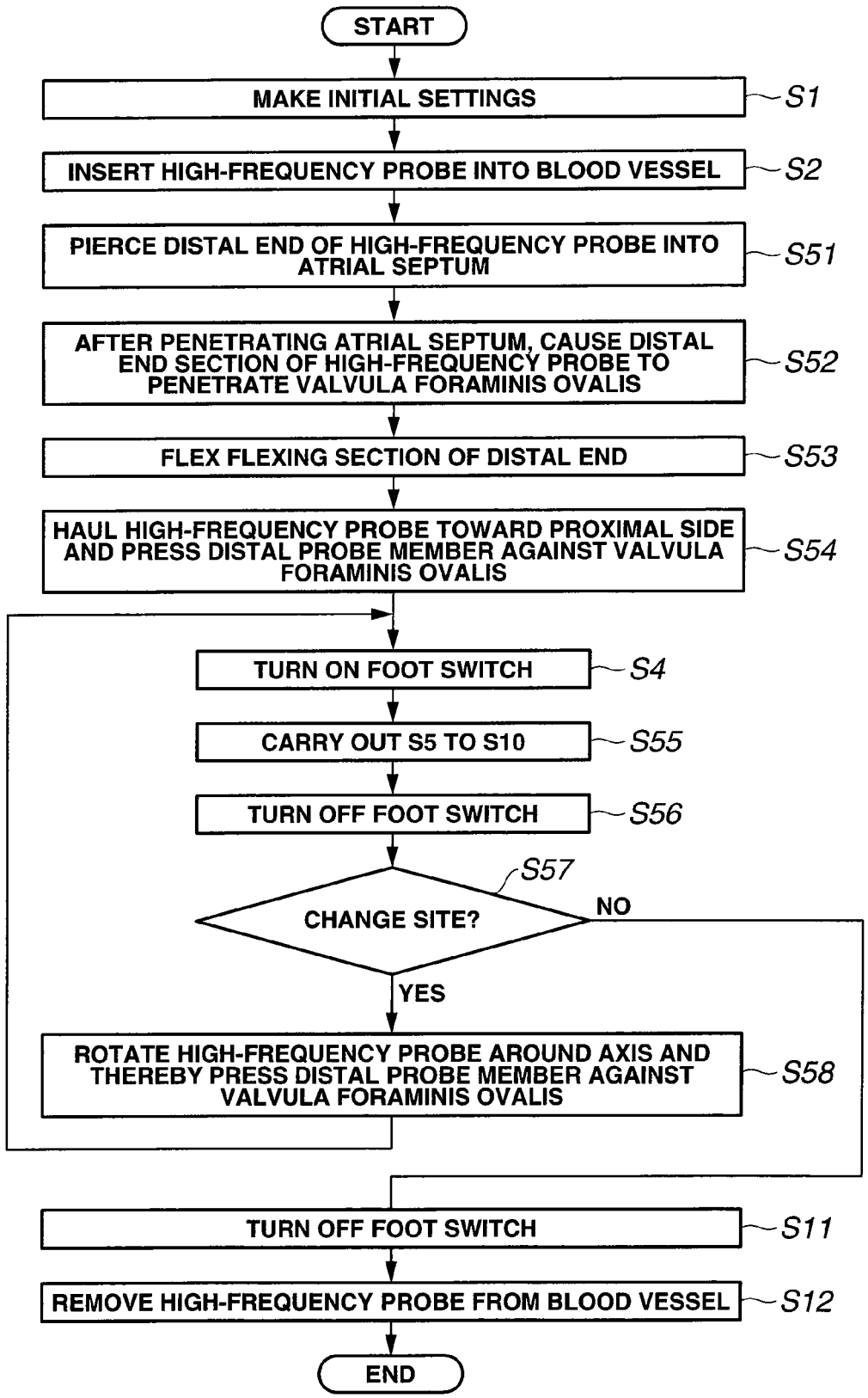

Steps S1 and S2 in FIG. 17 are the same as in FIG. 7. In Step S3 according to the first embodiment, the surgeon positions the electrode section 3 at the distal end of the high-frequency probe 2 in the PFO 31 between the atrial septum 34a and valvula foraminis ovalis 35.

On the other hand, according to the present embodiment, as shown in Step S51, the surgeon pierces the pointed distal end section 62a of the high-frequency probe 2B into the atrial septum 34a. After the distal end section 62a of the high-frequency probe 2B is pierced into the atrial septum 34a, as shown in Step S52, the surgeon causes the distal end section 62a of the high-frequency probe 2B to penetrate the valvula foraminis ovalis 35 of the PFO 31 located adjacent to the atrial septum 34a. That is, the surgeon causes the distal end of the high-frequency probe 2B to penetrate the atrial septum 34a and valvula foraminis ovalis 35 to reach the left atrium.

Figure 18:
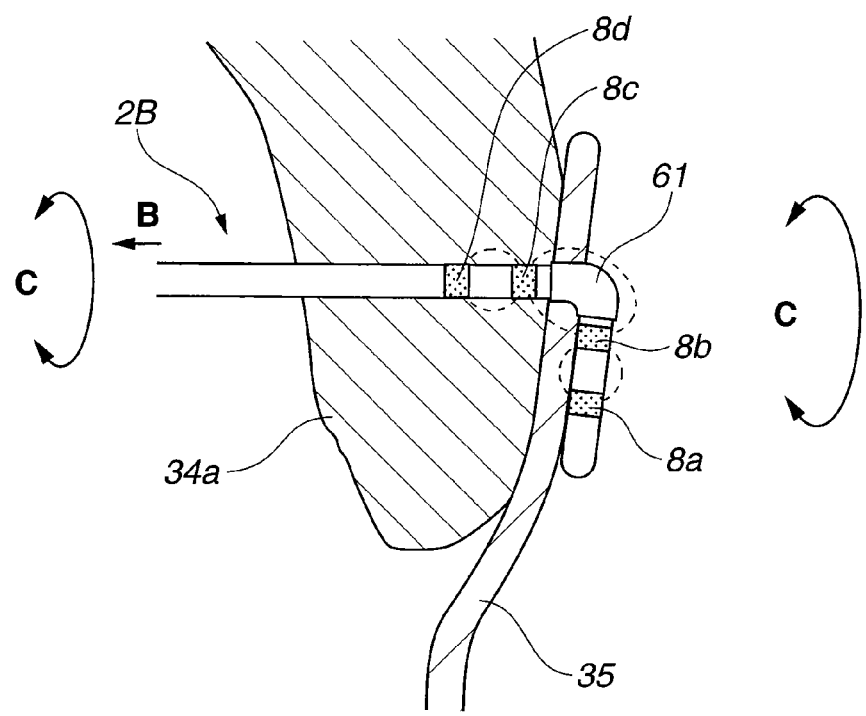

Next, in Step S53, by operating the operation knob 64, the surgeon hauls the wire 68, thereby flexing the flexing section 61, for example, by approximately 90 degrees, and pulls the high-frequency probe 2B toward the proximal side as indicated by arrow B in FIG. 18. Then, the surgeon presses the flexed distal probe member 62 against an outer surface of the valvula foraminis ovalis 35 of the PFO 31. A resulting state is shown in FIG. 18.

When the flexing section 61 is flexed by approximately 90 degrees and the high-frequency probe 2B is pulled toward the proximal side, the electrodes 8a and 8b on the distal probe member 62 are placed in close contact or pressing contact with the surface of the valvula foraminis ovalis 35, which is placed in close contact or pressing contact with the atrial septum 34a as well. In this way, the PFO 31 is brought into close contact state.

With the electrodes 8a and 8b on the distal probe member 62 placed in close contact or pressing contact with the surface of the valvula foraminis ovalis 35, the surgeon turns on the foot switch 5 as shown in Step S4.

Subsequently, Steps S5 to S10 in FIG. 7 are carried out. Steps S5 to S10 in FIG. 7 correspond to Step S55 in FIG. 17. Through Steps S5 to S10, high-frequency power is supplied to between electrodes 8a and 8b, between electrodes 8b and 8c, and between electrodes 8c and 8d to carry out the high-frequency cauterization procedure. In FIG. 18, flow of high-frequency currents caused by high-frequency power is indicated by dotted lines.

As shown in FIG. 18, the surgeon can cauterize the living tissue of the PFO 31 from the side of the valvula foraminis ovalis.

Next, in Step S56, the surgeon turns off the foot switch 5. Next, in Step S57, the surgeon determines whether to continue the procedure by changing the site to be treated.

To continue the procedure by changing the site, as shown in Step S58, the surgeon rotates the high-frequency probe 2B by an appropriate angle (indicated by symbol C in FIG. 18) around an axis of the high-frequency probe 2B, pulls the high-frequency probe 2B toward the proximal side, and thereby presses the distal probe member 62 against the surface of the valvula foraminis ovalis 35.

In this case, the surgeon may stop hauling, reduce flexion amount (i.e., reduce a pressing force), rotate the high-frequency probe 2B, and thereafter may increase the amount of flexing again, pull the high-frequency probe 2B toward the proximal side, and thereby press the distal probe member 62 against the surface of the valvula foraminis ovalis 35. The rotation direction of the high-frequency probe 2B around the axis, indicated by symbol C in FIG. 18, may be either clockwise or counterclockwise.

After Step S58, the surgeon returns to Step S4 where the surgeon turns on the foot switch 5 to carry out Steps S55 to S57. To continue the procedure by further changing the site, the surgeon returns to Step S4 after Step S58.

When the surgeon determines to have carried out the procedure over a wide area by changing the site, the surgeon goes from Step S58 to Step S11. Then, the surgeon turns off the foot switch 5 in the same manner as described with reference to FIG. 7, and finished the process after Step S12.

According to the present embodiment, by repeating cauterization by rotating the high-frequency probe 2B, the surgeon can carry out the procedure for closing the PFO 31 over a wide fan-shaped or circular area around a punctured (penetrated) site.

That is, the surgeon can carry out the high-frequency cauterization procedure over a wide area of the atrial septum 34a and valvula foraminis ovalis 35 which are living tissues forming the PFO 31, improving therapeutic effects of closure.

Figure 19:
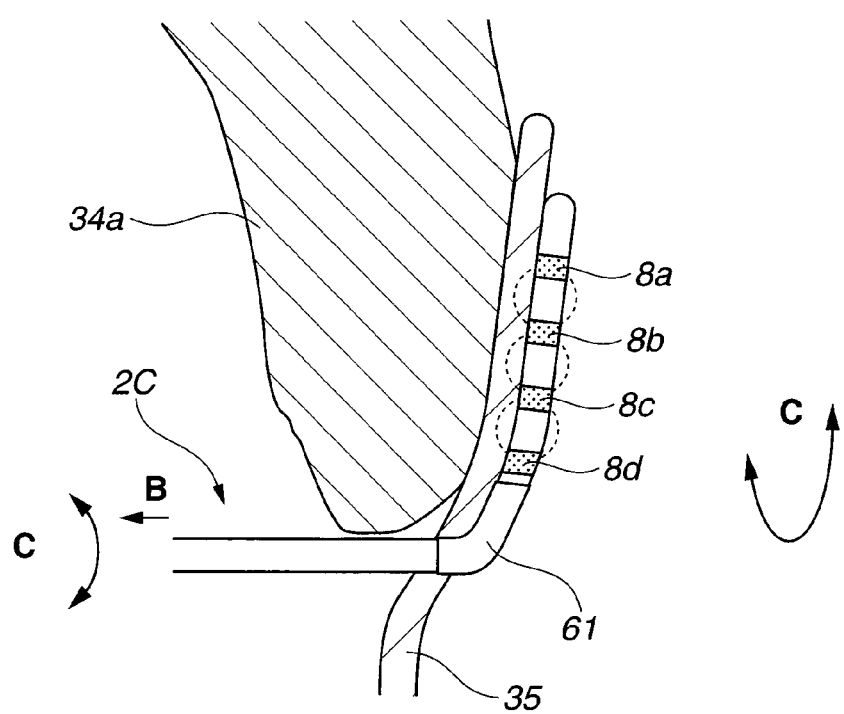

Incidentally, the location of the flexing section 61 according to the present embodiment may be changed. In the case of the high-frequency probe 2B shown in FIG. 14, the flexing section 61 is installed near the center (in the longitudinal direction) of the electrode section 3. The flexing section 61 may be installed adjacent to a proximal end of the electrode section 3. FIG. 19 shows the situation where the PFO 31 is treated by surgical method different from the present embodiment using a high-frequency probe 2C according to a variation.

Figure 20:
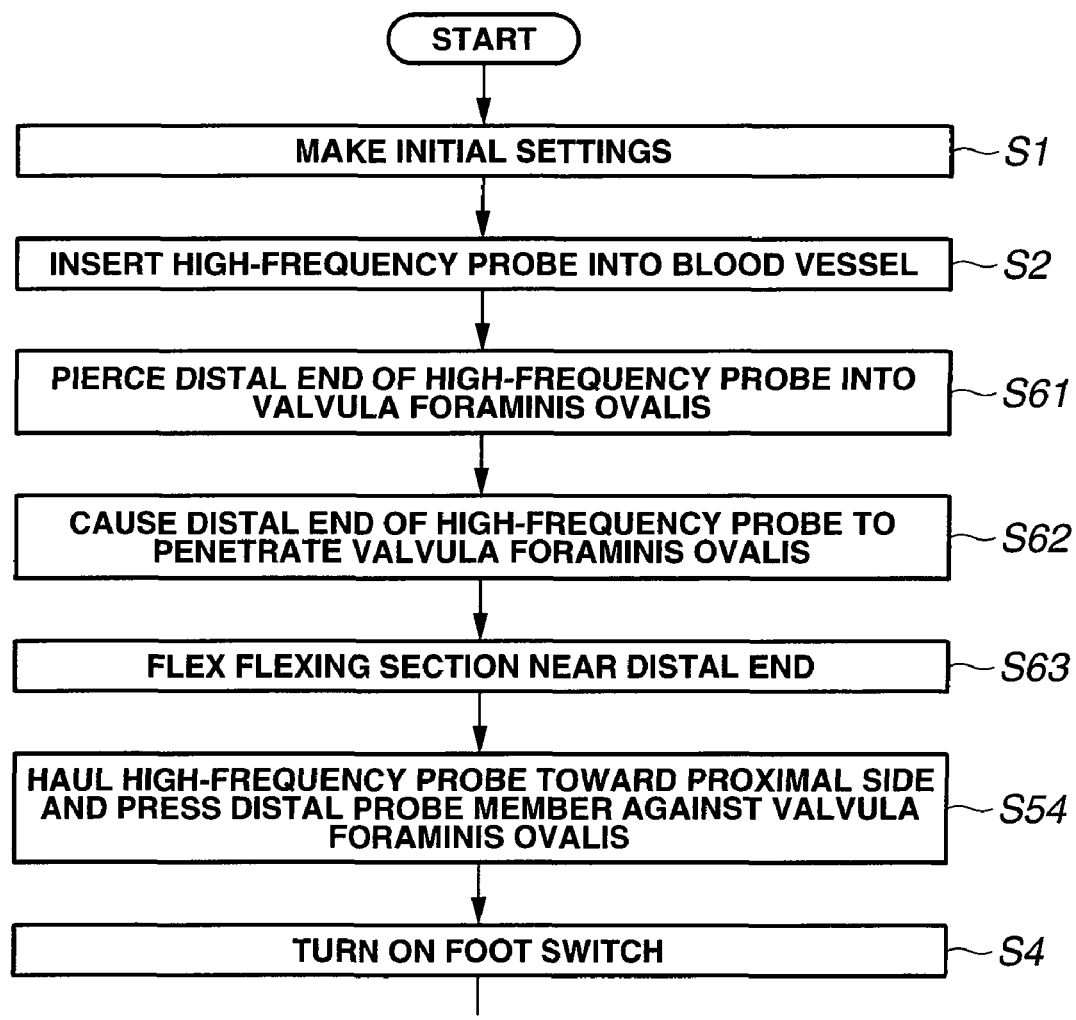
FIG. 20 is a flowchart showing part of procedures of a high-frequency surgical method according to a variation.

Part of the surgical method is shown in FIG. 20. In the surgical method shown in FIG. 20, Steps S51 to S53 according to the surgical method in FIG. 17 are replaced by Steps S61 to S63.

After Step S2, the surgeon pierces a distal end of the high-frequency probe 2C into the valvula foraminis ovalis 35 by traversing near an end of the atrial septum 34a as shown in Step S61 without piercing the distal end of the high-frequency probe 2C into the atrial septum 34a.

Next, as shown in Step S62, the surgeon causes the distal end of the high-frequency probe 2C to penetrate the valvula foraminis ovalis 35 all the way to the left atrium. With the present surgical method, the distal end of the high-frequency probe 2C is made to reach the left atrium through the atrial septum 34a. Regarding penetration length, it is recommended that the flexing section 61 be inserted approximately halfway.

Then, as shown in Step S63, the surgeon flexes the flexing section 61 provided near the distal end. In this case, the surgeon flexes the distal probe member equipped with the electrode section 3 toward the PFO 31 (to the upper side in FIG. 19), the distal probe member being located on the more distal side than the flexing section 61.

Then, as shown in Step S54, the surgeon hauls the high-frequency probe 2C (kept flexed) toward the proximal side (as indicated by arrow B in FIG. 19) and presses the distal probe member, located on the more distal side than the flexing section 61, against the outer surface of the valvula foraminis ovalis 35.

A resulting state is shown in FIG. 19. The rest of the process is much the same as FIG. 17. The surgeon turns on the foot switch 5 as shown in Step S4 to carry out Step S55. Consequently, high-frequency currents flow between electrodes 8a and 8b, between electrodes 8b and 8c, and between electrodes 8c and 8d as indicated by dotted lines in FIG. 19, allowing the surgeon to treat the living tissue of the PFO 31.

To continue the procedure, the surgeon goes from Step S57 to Step S58 as shown in FIG. 17. Then, the surgeon rotates the high-frequency probe 2C by an appropriate angle around the axis as indicated by arrows C in FIG. 19, hauls the high-frequency probe 2C toward the near side, and presses the distal probe member against the outer surface of the valvula foraminis ovalis 35. Then, the surgeon repeats the procedure by changing the site, as described above.

The method shown in FIGS. 19 and 20 also allows the surgeon to carry out the high-frequency procedure for closing the PFO 31 over a wide area of the living tissue of the PFO 31.

Whereas with the surgical method shown in FIGS. 17 and 18, the high-frequency procedure is carried out by changing the place pressed by a distal side of the flexing section 61 in such a way as to cover the entire circumference, the surgical method shown in FIGS. 19 and 20 is carried out by changing the place pressed by the distal side of the flexing section 61 in such a way as only to cover, for example, approximately half the circumference such as the upper half in FIG. 19.

Either method allows a wide area to be cauterized, providing high therapeutic effects.

According to the present embodiment, since the electrode section on the distal side of the high-frequency probe are placed in close contact with the living tissue of the PFO 31 and high-frequency currents are passed in this state, it is possible to effectively carry out the cauterization procedure for closing the PFO 31, improving therapeutic effects.

Figure 21:
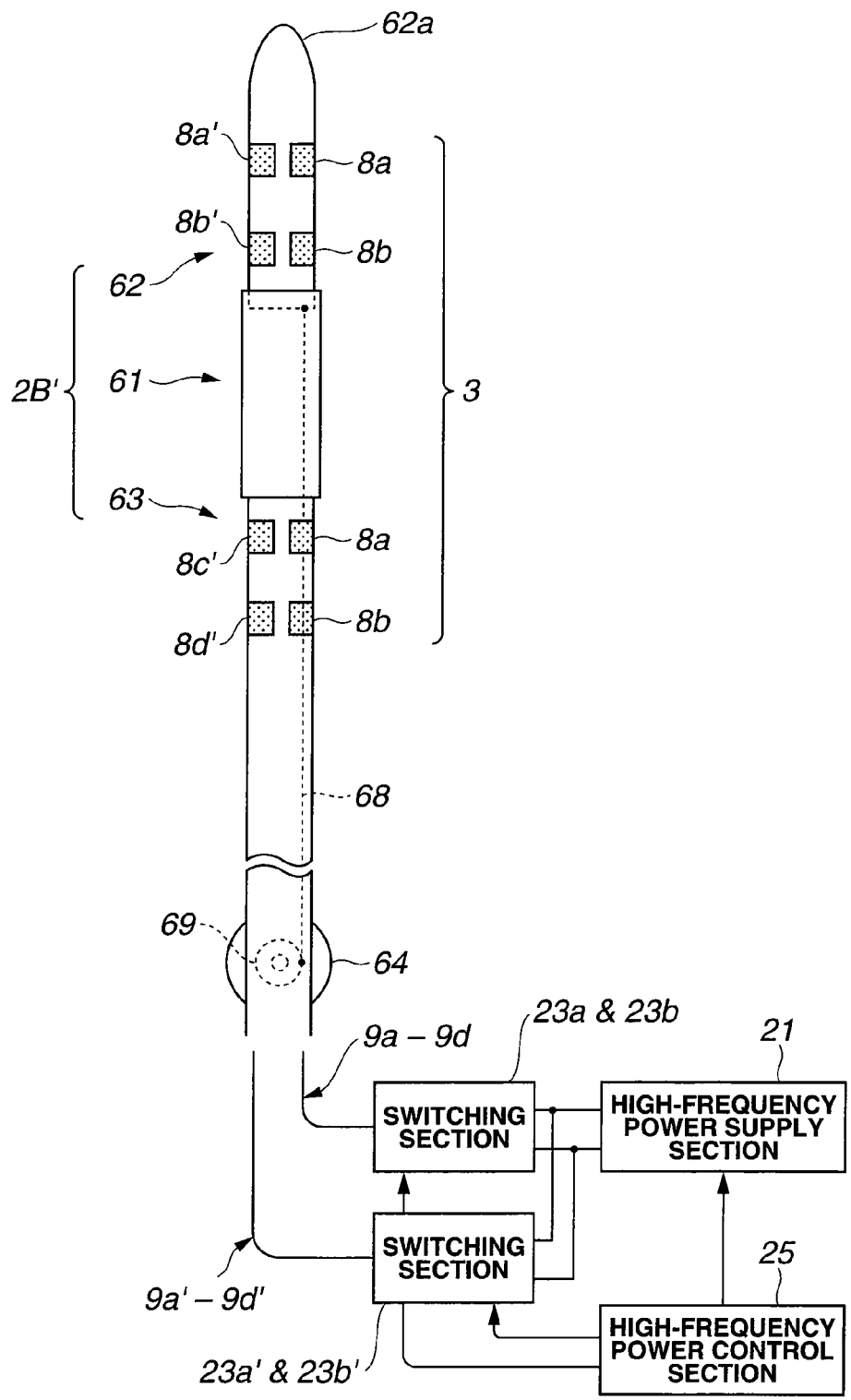
FIG. 21 is a diagram showing a configuration of another high-frequency probe.

Incidentally, in the high-frequency probe 2B shown in FIG. 14, each electrode 8i configuring the electrode section 3 is provided around the entire circumference of the high-frequency probe 2B, but each electrode 8i may be divided in the circumferential direction as shown in FIG. 21.

With a high-frequency probe 2B' in FIG. 21, each electrode 8i in FIG. 14 is divided into two (denoted by 8i and 8i' for the sake of simplicity) in two directions: the flexing direction of the flexing section 61 (rightward in FIG. 21) and the direction opposite to the flexing direction. Incidentally, the electrode 8i may be divided into three rather than two.

The lead wire 9i connected to each electrode 8i is connected to the high-frequency power supply section 21 via the switching sections 23a and 23b as shown in FIG. 10 and the like. In FIG. 21, the switching sections 23a and 23b are illustrated together, being denoted by 23a & 23b.

The lead wire 9i' connected to each electrode 8i' is also connected to the high-frequency power supply section 21 via switching sections 23a' and 23b' similar in configuration to the switching sections 23a and 23b. In FIG. 21, the switching sections 23a' and 23b' are illustrated together, being denoted by 23a' & 23b'.

The high-frequency power control section 25 controls operation of the switching sections 23a' and 23b' as well as the switching sections 23a and 23b. That is, the high-frequency power control section 25 also performs switching control of multiple electrodes 8i and 8i' formed in the circumferential direction of the high-frequency probe 2B', to selectively activate the electrodes 8i and 8i'.

The high-frequency power control section 25 may activate the switching sections 23a and 23a' in sync with the switching sections 23b and 23b', making it possible to use the electrodes 8i and 8i' divided in the circumferential direction as a single electrode formed around the entire circumference in the circumferential direction. This configuration will produce the same effects as the configuration in FIG. 14.

By making settings using the setting section 12, the surgeon can widely select the electrodes to be supplied with high-frequency power, via the high-frequency power control section 25.

For example, to carry out a procedure such as shown in FIG. 19, based on user selections, pairs of electrodes are selected in sequence from the electrodes 8a to 8d formed on the side flexed by the flexing section 61. That is, pairs of electrodes are selected in sequence from the electrodes 8a to 8d placed in pressing contact with the valvula foraminis ovalis 35. On the other hand, the electrodes 8a' to 8d' which are formed on the side opposite to the side flexed by the flexing section 61 and are out of contact with the valvula foraminis ovalis 35 are not selected.

The procedure carried out in this way makes it possible to treat the living tissue of the PFO 31 effectively.

Incidentally, although in the high-frequency probe 2B' in FIG. 21, the electrodes 8i and 8i' are formed in such a way as to divide the entire circumference in the circumferential direction into two parts, an electrode may be formed only in part of the entire circumference. The present invention includes, for example, a configuration which contains only one of the electrodes 8i and 8i' in FIG. 21, specifically only the electrode 8i.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A high-frequency surgical method for closure of patent foramen ovale, the high-frequency surgical method using a high-frequency probe to close the patent foramen ovale in a heart by application of high-frequency power, comprising:
 a piercing step of piercing a distal end of the high-frequency probe, which has passed through a blood vessel, from atrial septum through valvula foraminis ovalis, adjacent to the atrial septum;
 a flexing step of flexing a flexing section installed near the distal end of the high-frequency probe by operating from a proximal end of the high-frequency probe;
 a hauling step of hauling the high-frequency probe toward a proximal side so as to cause a flexed part of the flexing section to contact a tissue of the valvula foraminis ovalis with the flexing section kept flexed; and
 a supplying step of selecting at least different combinations of electrodes, a plurality of times, from among three or more electrodes installed at the distal end of the high-frequency probe and supplying high-frequency power for treatment to the selected electrodes.

2. The high-frequency surgical method for closure of patent foramen ovale according to claim 1, further comprising, after the supplying step, a rotating step of rotating the distal end of the high-frequency probe by a predetermined angle around an axis of the high-frequency probe and keeping the distal end of the high-frequency probe at the predetermined angle, wherein
 the supplying step is carried out again after the rotating step.

3. The high frequency surgical method for closure of patent foramen ovale according to claim 1, further comprising a step of controlling a period of time for which the high-frequency power is supplied to the two electrodes.

4. A high-frequency surgical method for closure of patent foramen ovale, the high-frequency surgical method using a high-frequency probe to close the patent foramen ovale in a heart by application of high-frequency power, comprising:
 a puncturing step of puncturing valvula foraminis ovalis adjacent to the atrial septum with a distal end of the high-frequency probe from the atrial septum for treatment by the application of high-frequency power;
 a penetrating step of causing a distal end of the high-frequency probe, punctured into the valvula foraminis ovalis by the puncturing step, to penetrate the atrial septum and the valvula foraminis ovalis;
 a flexing step of flexing a flexing section installed near the distal end of the high-frequency probe by operating from a proximal end of the high-frequency probe;
 a hauling step of hauling of the high-frequency probe toward a proximal side so as to cause a flexed part of the flexing section to contact a tissue of the valvula foraminis ovalis with the flexing section kept flexed; and
 a supplying step of selecting at least different combinations of electrodes, a plurality of times, from among three or more electrodes installed at the distal end of the high-frequency probe and supplying high-frequency power for treatment to the selected electrodes.

5. The high-frequency surgical method for closure of patent foramen ovale according to claim 4, further comprising, after the supplying step, a rotating step of rotating the distal end of the high-frequency probe by a predetermined angle around an axis of the high-frequency probe and keeping the distal end of the high-frequency probe at the predetermined angle, wherein
 the supplying step is carried out again after the rotating step.

6. The high frequency surgical method for closure of patent foramen ovale according to claim 4, further comprising a step of controlling a period of time for which the high-frequency power is supplied to the two electrodes.

* * * * *